United States Patent [19]

Sramek

[11] Patent Number: 5,103,828

[45] Date of Patent: Apr. 14, 1992

[54] SYSTEM FOR THERAPEUTIC MANAGEMENT OF HEMODYNAMIC STATE OF PATIENT

[75] Inventor: Bohumir Sramek, Irvine, Calif.

[73] Assignee: BoMed Medical Manufacturing, Ltd., Irvine, Calif.

[21] Appl. No.: 622,322

[22] Filed: Nov. 28, 1990

Related U.S. Application Data

[63] Continuation of Ser. No. 219,990, Jul. 14, 1988, abandoned.

[51] Int. Cl.$^5$ .............................................. A61B 5/02
[52] U.S. Cl. .................................. 128/668; 128/693; 128/734
[58] Field of Search ............... 128/713, 734, 668, 693; 600/16, 17

[56] References Cited

U.S. PATENT DOCUMENTS

| Re. 30,101 | 9/1979 | Kubicek et al. | |
| 4,429,701 | 2/1984 | Goor et al. | 128/713 |
| 4,437,469 | 3/1984 | Djordjevich et al. | 128/713 |
| 4,450,527 | 5/1984 | Sramek | |
| 4,798,211 | 1/1989 | Goor | 128/668 |
| 4,807,638 | 2/1989 | Sramek | 128/713 |

OTHER PUBLICATIONS

"Why Should Cardiac Output Be Measured/Monitored,'" Customer Information Bulletin, May 20, 1986, pp. 1-13.

William C. Shoemaker, M.D., et al., "Therapy of Critically Ill Postoperative Patients Based On Outcome Prediction and Prospective Clinical Trials," *UCLA Medical Center*, Rev: Aug. 27, 1984, pp. 1-31.

*Primary Examiner*—Kyle L. Howell
*Assistant Examiner*—Robert L. Nasser, Jr.
*Attorney, Agent, or Firm*—Knobbe, Martens, Olson & Bear

[57] ABSTRACT

A therapeutic system provides a clinician with an appropriate course of treatment for a patient whose cardiovascular system is operating outside the normal range of values for the left cardiac work index (LCWI) and the systemic vascular resistance index (SVRI). The left cardiac work index and the systemic vascular resistance index are calculated from the cardiac index (CI) and mean arterial blood pressure (MAP) and are displayed as relative values so that the clinician can readily determine which of the vascular parameters are outside the normal range. Preferably, the cardiac index and the other cardiac parameters are measured by an electrical bioimpedance monitor that provides continuous dynamic measurement of the parameters. The left cardiac work index and the systemic vascular resistance index are calculated by a personal computer that displays the calculated parameters in an easily discernible manner.

38 Claims, 11 Drawing Sheets

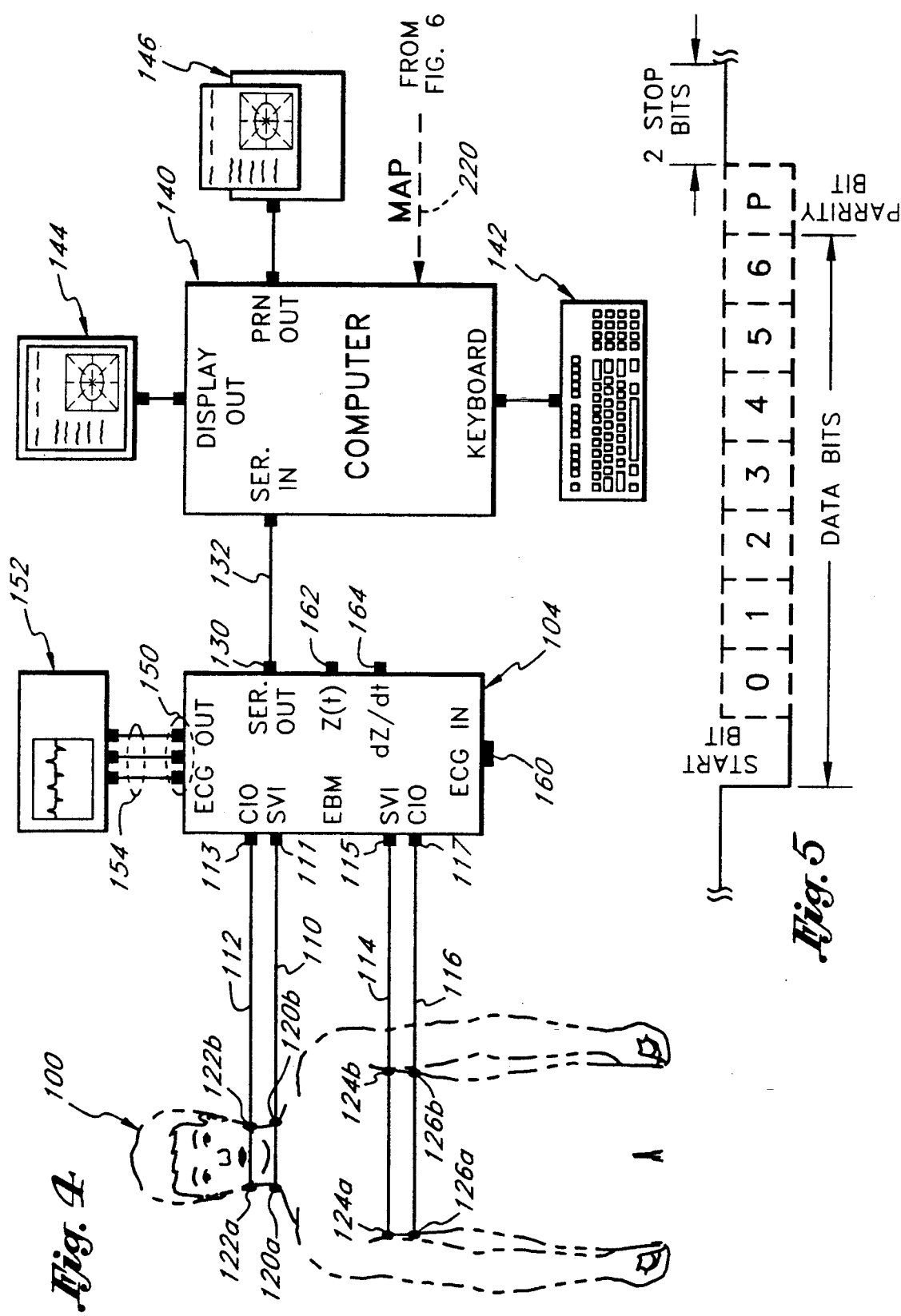

Fig. 9

.DOE_JOHN , male ,03 15 25 ,175cm ,123kg   ©1988 BoMed

HEMODYNAMIC / CARDIODYNAMIC DATA    HR = 60 beats/min

| | | 380 | 382 | | |
|---|---|---|---|---|---|
| GLOBAL FLOW | CI | 2.8 | 4.2 | | 2.7 L/min/m2 |
| PUMP PERFORMANCE | SI | 30 | 65 | | 46 mL/m2 |
| PRELOAD (volume) | EDI | 45 | 100 | | 96 mL/m2 |
| CONTRACTILITY (inotropy) | IC | .033 | .065 | | 0.032/sec |
| | ACI | 0.5 | 1.5 | | 0.89/sec2 |
| AFTERLOAD | SVRI | 1660 | 2580 | | 3870 F.Ohm/m2 |
| CARDIAC WORK | LCWI | 3.3 | 5.3 | | 5.0 kgm/m2 |
| PUMP EFFICIENCY | EF | 35 | 65 | | 47 % |
| THORACIC FLUIDS | TFC | .030 | .050 | | 0.033/Ohm |
| MEAN ARTER.PRESS | MAP | | 84 | 100 | 135 Torr |

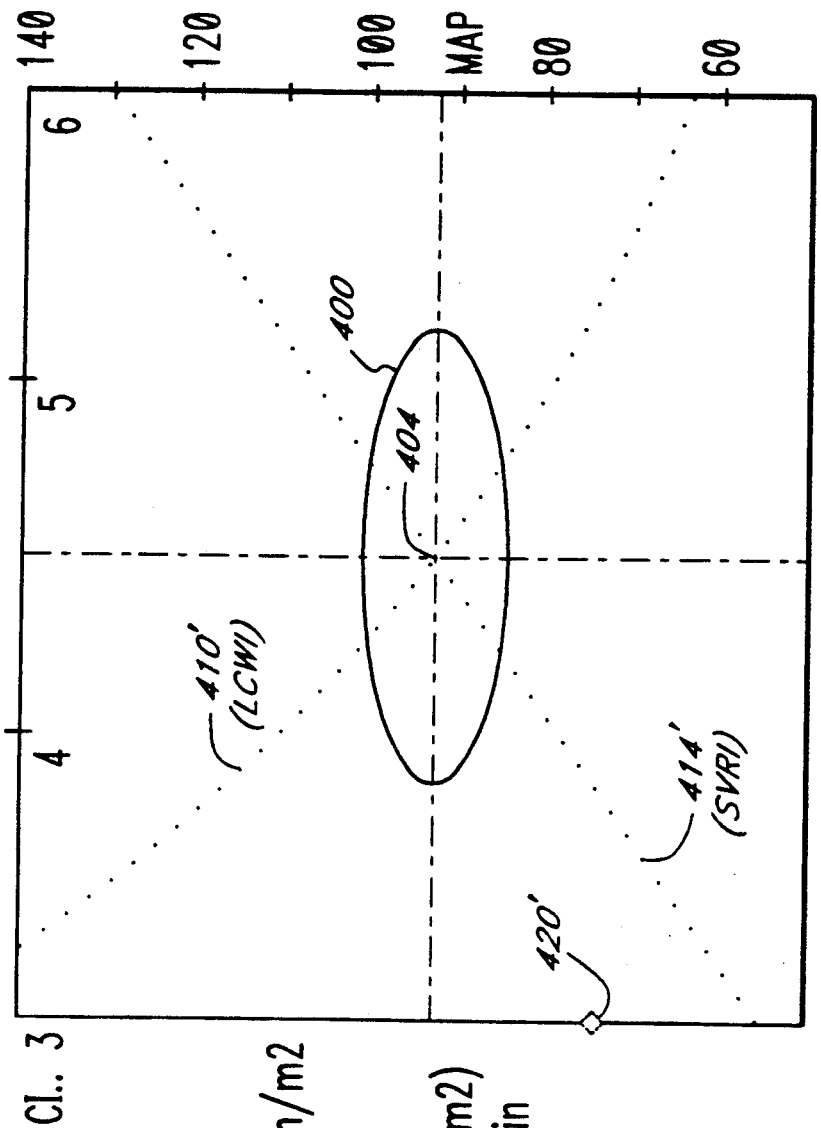

SYSTEM FOR THERAPEUTIC MANAGEMENT OF HEMODYNAMIC STATE OF PATIENT

This application is a continuation of application Ser. No. 219,990, filed July 14, 1988.

NOTICE REGARDING INCLUSION OF COPYRIGHTED MATERIAL

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to a method and apparatus for the non-invasive diagnosis and therapeutic management of patients having systemic hypertension or other critical illnesses, and, more particularly, to a method and apparatus for determining a therapy to achieve both a normotensive and normodynamic state or a selected stated dictated by conditions to increase the probability of survival after surgery, trauma, illness, or the like.

Hypertension is typically diagnosed through a non-invasive measurement of systolic and diastolic arterial pressure values by a sphygmomanometer, and by comparing the obtained "blood pressure" values to values considered "normal" for that particular patient taking into consideration the sex, age and body habitus. Once diagnosed, hypertension today is predominantly treated by prescription of any of a variety of classes of drugs which are pharmacologically capable of reducing the measured blood pressure value. Hypertension is then considered under control when the measured arterial pressures reach the normal range.

Although the use of such single modality therapy is generally quite successful in achieving the desired variation in the measured blood pressure, it does not take into account the patient's status with regard to more important hemodynamic parameters, such as cardiac output. Hypertensive drugs can be prescribed which have the additional and unmeasured effect of simultaneously lowering cardiac output. Thus, notwithstanding attainment of the normotensive end goal of therapy, important hemodynamic deviations can remain, or even be induced by the prescribed therapy. The resulting diminished perfusion could be reasons for so-called side effects of hypertension therapy, such as dizziness, impotence and general down feeling, which the patient typically did not experience prior to diagnosis and traditional treatment of hypertension. Hence, current hypertension therapy could lead to prolonged duration of the treatment, higher cost to the patient and/or medical insurance carrier, adverse side effects resulting in patient's noncompliance, and general lowering of the patient's quality of life.

The importance of precise differentiation between normotensive therapy and effects on the hemodynamic state have recently been underscored by the work of W. C. Shoemaker, M.D., Department of Surgery, UCLA Medical Center, in the postoperative critically ill patient. While studying postoperative, high-risk, critically ill survivors and non-survivors, Shoemaker found that, in general, the survivors' cardiovascular systems maintained mean arterial pressure at a normotensive level while increasing their global blood flow to a cardiac index of greater than 4.5 liters/min/m$^2$ and maintaining it at that level throughout the postoperative period.

In contrast, the non-survivors did not experience increased global blood low during the postoperative period. The non-survivors generally were normotensive and maintained blood flow at a cardiac index of 3.5 liters/min/m$^2$ which is considered normal for healthy adults.

The surgical wound requires significantly increased perfusion to facilitate healing and the removal of fluids. Thus, in order to maintain adequate perfusion of all organs, the global blood flow must increase. If this condition is not met, the brain will reduce flow to selected organs in order to maintain increased perfusion of the surgical site. The organs inadequately perfused will eventually fail. Shoemaker found that the mean time at which the deaths of non-survivors occurred was approximately 90 hours postoperatively as a result of single or multiple organ failure.

Subsequently, in a controlled study, Shoemaker proved that in patients who are not in hyperdynamic sepsis and whose cardiovascular systems cannot increase the level of global blood flow to a desired hyperdynamic level, proper immediate postoperative management through volume expansion, positive inotropic support and peripherally vasoactive therapy, resulting in a cardiac index greater than 4.5 liters/min/m$^2$ and normotension (mean arterial blood pressure approximately equal to 92 Torr), will substantially increase their chances to survive.

The implementation of the foregoing therapeutic goal has the potential for a dramatic reduction of postoperative mortalities, estimated to be approximately 400,000 annually in the U.S. alone.

SUMMARY OF THE INVENTION

There has been provided in accordance with one aspect of the present invention a method of achieving a preselected hemodynamic state in a subject mammal, typically a human patient. The preselected hemodynamic state may be a state of normovolemia, normoinotropy and arterial normocapacitance, although the preselected state may be another hemodynamic state, if indicated by the circumstances surrounding diagnosis and treatment. The method comprises the steps of first determining the mean arterial pressure of the patient and then measuring the cardiac index of that patient. Left cardiac work index (LCWI) is determined based upon the foregoing measured values, in accordance with the formula:

$$LCWI = (MAP - PAOP) \times CI \times K$$

wherein MAP represents mean arterial pressure, PAOP represents pulmonary artery occluded pressure, CI represents cardiac index and K is a constant. Typically, PAOP may be assumed to be approximately 6 Torr. The patient's systemic vascular resistance index (SVRI) is additionally determined utilizing the measured values of mean arterial pressure and cardiac index, according to the formula:

$$SVRI = \frac{(MAP - CVP) \times 80}{CI}$$

wherein CVP is central venous pressure, which typically may be assumed to be approximately 3 Torr. The obtained LCWI and SVRI values are thereafter compared to the values desired to be obtained in the patient, and a therapeutic dose of a pharmacologically active material is administered for altering these values to achieve the preselected hemodynamic state. In a case where the preselected hemodynamic state in an adult patient comprises arterial normocapacitance, the pharmacologically active material comprises a vasodilator if the systemic vascular resistance index exceeds about 2030 dyn.sec/cm$^5$m$^2$. Alternatively, if the systemic vascular resistance index is less than about 2030 dyn.sec/cm$^5$m$^2$, the pharmacologically active material comprises a vasoconstrictor.

In a case in which the end goal of therapy is achieving normovolemia and normoinotropy, the pharmacologically active material comprises one which will have a volume expansion and/or positive inotropic effect if the left cardiac work index is less than about 4.35 kg.m/m$^2$. Alternatively, volume reduction and/or negative inotropic therapy will be indicated in a patient having a left cardiac work index in excess of about 4.35 kg.m/m$^2$.

Further features and advantages of the present invention will become apparent from the Detailed Description of Preferred Embodiments which follows, when considered together with the attached figures.

BRIEF DESCRIPTION OF THE DRAWINGS

FIG. 4 illustrates a schematic representation of an electronic system to assist in providing the diagnostic and therapeutic information in accordance with the method of the present invention.

FIG. 5 illustrates an exemplary data format for the serial output transmitted from the exemplary NCCOM®3-R7 electrical bioimpedance monitor to the computer in FIG. 4.

FIG. 9 illustrates an exemplary screen display that utilizes bar graphs to display the parameters of the hemodynamic status of a patient's cardiovascular system for use in diagnostic evaluation of a patient.

FIG. 12 illustrates the cartesian graph screen display of FIG. 11 for the same patient and the same input parameters but with the coordinates of the graph adjusted for a therapeutic goal of increased oxygen perfusion, showing that, for this therapeutic goal, the patient has an increased percentage of relative hypovolemia and/or hypoinotropy and has relative arterial hypocapacitance.

DETAILED DESCRIPTION OF PREFERRED EMBODIMENTS

Figure 1:
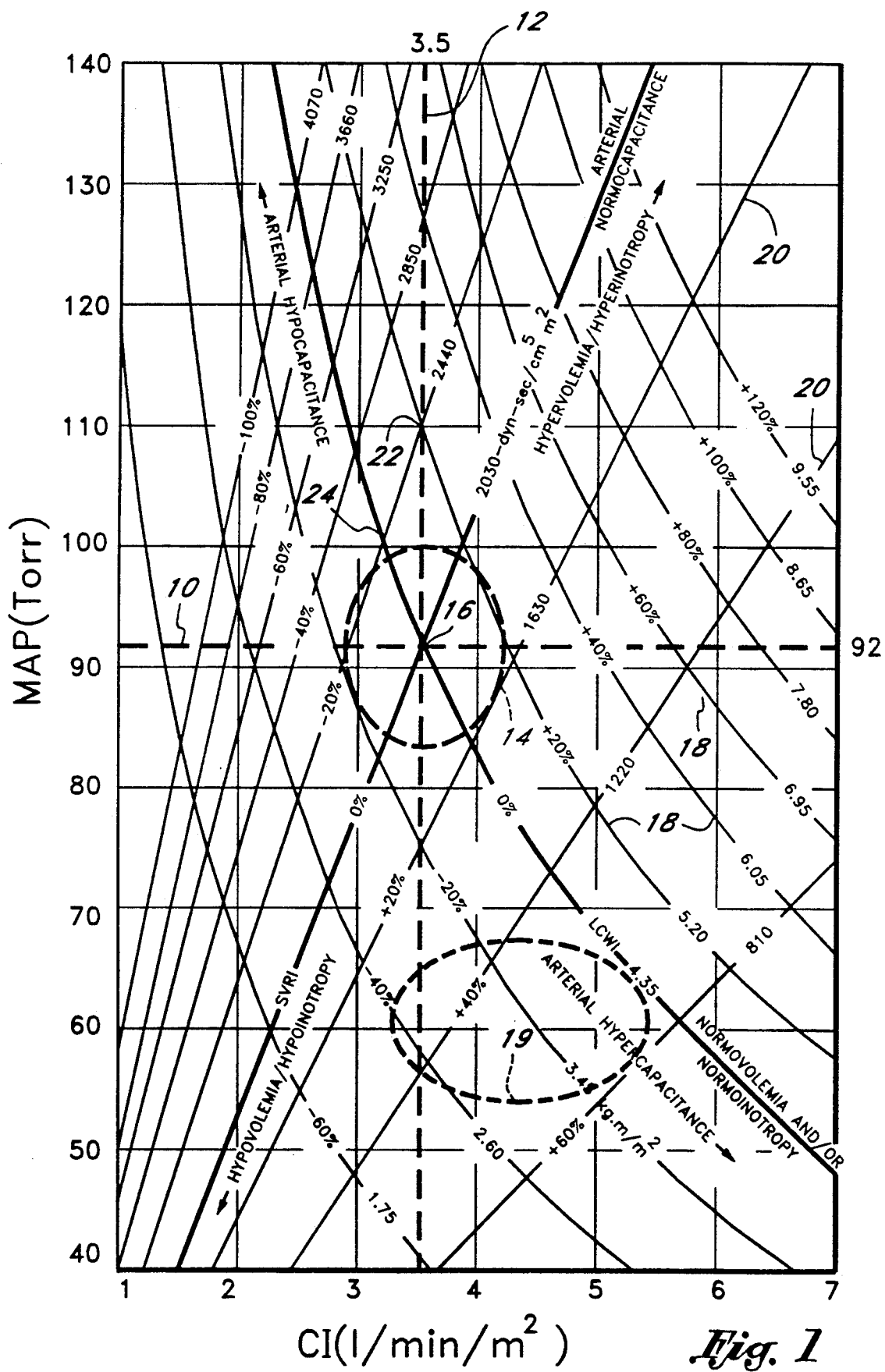
FIG. 1 illustrates the interrelationship between cardiac index, mean arterial pressure, systemic vascular resistance index and left cardiac work index in a human adult.

The primary function of the cardiovascular system is transport of oxygen. Pulsatile pressure having a mean component (mean arterial pressure or MAP) develops as a byproduct of the viscosity of blood pushed out of the left ventricle and through the vasculature system which is characterized by a systemic vascular resistance (SVR). The systemic vascular resistance and mean arterial pressure are related such that in the absence of corrective mechanisms, a reduction in SVR through vasodilatation will result in a reduction in pressure. However, it is generally recognized that the supply of oxygen to all tissue cells is a function of global blood flow, i.e., cardiac output, and not blood pressure as will become apparent.

Determination of MAP is typically achieved using a sphygmomanometer to directly determine systolic and diastolic pressure, and solving the following equation:

$$MAP = \frac{SYSTOLIC - DIASTOLIC}{3} + DIASTOLIC \quad (1)$$

MAP values may also be measured and displayed directly on automated blood pressure instruments using oscillometric principles.

There currently exist about eight practical methods of measuring cardiac output, including three indicator dilution methods (known as FICK, dye and thermodilution), three methods which allow visualization of heart chambers and a subsequent calculation of stroke volume and cardiac output (cine-angiography, gated pool radionuclides, echocardiography) and two other methods (Doppler ultrasound and--electrical bioimpedance). The only absolutely accurate blood flow measurement method, not mentioned above, is a calibrated cylinder to collect blood and a stopwatch. Of course, each of the foregoing methods is characterized by a unique balance of accuracy, invasive/non-invasive nature, and patient risk, as will be appreciated by one of skill in the art.

Although any of the foregoing known methods of determining cardiac output may by used, the mechanics of each being well known in the art, it is preferred in the context of the present invention to non-invasively and instrument such as the NCCOM® 3-R7 manufactured by BoMed® Medical Manufacturing Ltd. in Irvine, Calif., which is the subject matter of U.S. Pat. No. 4,450,527, which is incorporated herein by reference. This instrument has been determined to exhibit the same accuracy as any of the available alternative methods, while accruing the substantial advantage of being a non-invasive technique.

In addition to determining cardiac output, several additional parameters can be measured non-invasively utilizing the NCCOM ® 3-R7, as a result of its use of Thoracic Electrical Bioimpedance (TEB) technology. TEB measures total electrical impedance of the thorax which is called TFI (Thoracic Fluid Index) and which is volume dependent. TFI has a normal range in males between 20 and 33 Ohms and in females between 27 and 48 Ohms. A lower TFI value indicates an excess of fluids (more conductive thorax).

TEB also measures two parameters which are related to measurement of contractility. Index of Contractility, (IC), is a volume-dependent measure of the contractile state and ACI (Acceleration Index) is a volume-independent measure of the inotropic state. The normal range for IC in a human adult falls between about 0.033 to about 0.065/sec, and the normal range for ACI is between about 0.5 and about $1.5/sec^2$. TEB measurements may conveniently be performed using the BoMed NCCOM ® 3-R7, and provide useful supporting data as will be discussed.

Once MAP and CI (cardiac index, a normalized value of cardiac output, as will be explained below are known, two additional important hemodynamic parameters can be determined. The first is the systemic vascular resistance index (SVRI) defined by the arithmetic ratio of the arterial-venous pressure difference and an indexed blood flow in accordance with the following equation:

$$SVRI = \frac{(MAP - CVP) \times 80}{CI} \quad (2)$$

In this equation, CVP is central venous pressure measured in Torr, 80 is a constant of proportionality and CI is the cardiac index. Since the value of cardiac output (CO) is a direct function of body mass, its normalized value, e.g., cardiac index (CI) is a more appropriate indicium for assessing adequacy of perfusion. Similarly, with systemic vascular resistance being flow dependent and, therefore, body size-dependent, its direct use is unhelpful for absolute quantification of the normal levels of arterial capacitance. Thus, its indexed value, SVRI, will be discussed herein. If cardiac index (CI) is used as in Equation (2), the equation will directly provide the indexed parameter SVRI. The NCCOM ® 3-R7, for example, allows a clinician to enter either the patient's body weight or the patient's body surface area to provide a basis for calculating the indexed outputs.

The data obtained through Equation (2) will not be subject to a significant error if CVP=3 Torr is assumed to be a typical value in the usual patient. In some cases, of course, the CVP can vary from as low as about 0 (zero) Torr to as high as about 10 Torr under different hemodynamic conditions. Minor variations from 3 Torr are generally insignificant since CVP is subtracted from the much larger MAP which may range from approximately 93 Torr in the normotensive patient to as high as 120 Torr as in Example 2 (described hereinafter), or higher in a hypertensive patient.

A second important hemodynamic parameter that can be calculated once MAP and CI are known, is the left cardiac work index (LCWI) defined by the arithmetic product of the pump's pressure contribution and blood flow as expressed in the following equation:

$$LCWI = (MAP - PAOP) \times CI \times 0.0144 \text{ kg.m}/m^2 \quad (3)$$

wherein PAOP is pulmonary artery occluded pressure in Torr, CI is cardiac index in liters/min/m², and 0.0144 is a constant of proportionality. In the typical patient, the PAOP will be approximately 6 Torr, and this value may be ordinarily assumed without subjecting the data to any significant error. However, a patient's actual PAOP can vary sufficiently to justify determination of the actual PAOP value for use in Equation (3) under conditions of pump failure. In such a case, the actual PAOP can be determined invasively using a thermodilution catheter.

Depending upon oxygen demand, the heart has a capability to vary cardiac output by a factor of 10, all within the life-sustaining range, throughout which MAP is maintained by the brain at a fairly constant level due to several biofeedback mechanisms with different time constants. Thus, the brain continually re-evaluates Equation (2) to maintain MAP constant, and a decrease in SVRI (increase in global oxygen demand) must be met by an equal percentage increase of CI (increase in oxygen delivery) in order to maintain MAP constant. Thus, the brain attempts to maintain. MAP constant by simultaneously varying SVRI by vasoactivity and output of the pump by heart rate, preload, contractility and afterload.

Essential hypertension, as generally understood today, is probably caused by a gradual increase of stiffness of arterial walls which results in an increase in vascular impedance, or by a gradual decrease of vascular capacitance, e.g., gradual vasoconstriction. Both cases result in an increase of SVRI. In order to provide adequate perfusion, (which, for an adult is approximately 3.5 liters/min/m²), under conditions of an elevated SVRI, the brain must permit a rise in MAP to accommodate Equation (2). This is a hemodynamic explanation of essential hypertension.

Since, in the case of essential hypertension, the body must increase MAP in order to provide adequate perfusion, the worst choice of therapy would be to prescribe drugs to lower MAP (which the clinician can easily measure) and, unfortunately also simultaneously lower CI (which the clinician typically does not measure). The resulting diminished perfusion could be reasons for the so-called side effects of hypertension therapy including dizziness, impotence and general down feeling, which the patient often did not experience prior to institution of the hypertension therapy.

The end goal of essential hypertension therapy should therefore be to lower the blood pressure to an acceptable, e.g., normotensive level, while maintaining adequate perfusion. This cannot be accomplished by measuring mean arterial pressure alone, but must also involve the determination of the deviation, if any, from arterial normocapacitance and normovolemia and/or normoinotropy, based upon measured values for MAP and cardiac index.

The mutual interrelationships between MAP, CI, LCWI for the supine resting adult, defined by Equations (2) and (3) above, are illustrated in FIG. 1. Since MAP and CI can be directly measured, they become coordinates of the orthogonal system while LCWI and SVRI become the derived parameters. From this chart, the approximate values of LCWI and SVRI can be visually observed without the necessity of going through the foregoing equations.

The range of normal MAP, illustrated in FIG. 1 at numeral 10, and the range of normal CI 12 define two main perpendicular axes of an ellipse 14 encompassing the loci of all normotensive and normodynamic patients. The center 16 of the ellipse 14 represents an ideal mean-mean value and could be considered an appropriate end goal of therapy for patients whose data describes a point outside of the normal ranges. Since the ideal MAP and CI are described in terms of ranges, however, and not absolute values, the data derived from a normotensive and normodynamic patient will define a point on FIG. 1 which may be anywhere within ellipse 14. Ellipse 14 reflects the empirically derived data that $MAP_{mean}$ equals 92 Torr, with a range of normotension from about 84 to about 100 Torr depending on the hemodynamic state. In addition, the $CI_{mean}$ equals 3.5 liters/min/m$^2$, with a normodynamic range of from about 2.8 to about 4.2 liters/min/m$^2$ in the resting human adult depending upon the hemotensive state.

The LCWI lines 1B run from the upper left of FIG. 1 to the lower right. The particular LCWI lines (not illustrated) which are tangent to the ellipse 14 define the bounds of the normal range of LCWI for adult humans. The SVRI lines 20 run from the upper right of FIG. 1 to the lower left. Similarly, the particular SVRI lines (not illustrated) which are tangent to the ellipse 14 (not illustrated) define the bounds of the normal range of SVRI for human adults. Although literature-published data of normal ranges of LCWI and SVRI, based on demographic data collected by any particular author, can vary considerably, the following are believed representative of a significantly large population and have, therefore, been incorporated into FIG. 1: $LCWI_{mean}=4.35$ kg.m/m$^2$; normal LCWI range is between about 3.3 and 5.3 kg.m/m$^2$; $SVRI_{mean}=2030$ dyn.sec/cm$^5$m$^2$; and the normal SVRI range is between about 1660 and 2580 dyn.sec/cm$^5$m$^2$. For neonatal patients, the normal LCWI range is between about 2.5 and 4.0 kg.m/m$^2$, and the normal SVRI range is between about 950 and 1500 dyn.sec/cm$^5$m$^2$. Thus, for example, a subject's deviation from normal LCWI can be calculated utilizing the measured values of MAP and CI according to the formula:

$$\text{deviation} = \frac{(MAP - PAOP) \times CI \times K}{4.35 \text{ kg} \cdot \text{m/m}^2}$$

wherein PAOP represents pulmonary artery occluded pressure and K is a constant.

The loci of constant LCWI (the hyperbola 18) simultaneously represent the isovolemic and/or isoinotropic lines. Hence, the LCWI line passing through the center of the ellipse 14 (LCWI=4.35 kg.m/m$^2$) is the line of normovolemia and/or normoinotropy. A patient who is in the center of the normotensive and the normodynamic ranges is also normovolemic and normoinotropic.

The foregoing results from the fact that the heart is neither a constant volume nor a constant pressure pump. By circulating non-compressible fluid through the system which exhibits a given value of SVRI, it creates MAP with a certain level of arterial distention. For example, consider a patient exhibiting a starting state corresponding to point 16 on FIG. 1 wherein CI=3.5 liters/min/m$^2$, MAP=92 Torr, and SVRI=2030 dyn.sec/cm$^5$,$^2$. If the system would vasoconstrict to SVRI=2440 dyn.sec/cm$^5$m$^2$, MAP would increase in an attempt to maintain an adequate level of perfusion. If the circulation level would remain the same (CI=3.5 liters/min/m$^2$), MAP would increase to 110 Torr (point 22 on FIG. 1), causing additional arterial distention through an increase in intravascular pressure, hence an increase of volume. On the other hand, if the system would maintain the same volume while vasoconstricting to SVRI=2440 dyn.sec/cm$^5$m$^2$level, it would reach MAP=101 Torr (point 24 on FIG. 1) but would have to simultaneously decrease CI to 3.2 liters/min/m$^2$ LCWI=4.35 kg.m/m$^2$ is, therefore, a line of a constant volume.

Patients having an LCWI value lower than about 4.35 kg.m/m$^2$ are either hypovolemic or hypoinotropic, or a combination of both. Conversely, if the patient's LCWI value is higher than about 4.35 kg.m/m$^2$, the patient's heart is not only burning a greater amount of oxygen but the patient is also hypervolemic or hyperinotropic, or a combination of both. The volemic and inotropic status of a patient are masked by each other on Figure when considering the patient's MAP and CI alone. However, whether a deviation in LCWI is due to an abnormal volemic or inotropic state can be differentiated through consideration of the supporting TEB data, as illustrated in Example 1.

The LCwI hyperbolas 18 are marked in FIG. 1 both by their respective kg.m/m$^2$ value and by the percentage deviation from normovolemia and/or normoinotropy. The negative deviations represent hypovolemia and/or hypoinotropy, whereas the positive deviations represent hypervolemia and/or hyperinotropy. Thus, for example, where the deviation in LCWI has a component from abnormal volemia, normovelemia can be restored by increasing fluid volume if the deviation (as defined in the formula described above) from normal LCWI is less than 1.0, and decreasing fluid volume if the deviation from normal LCWI is greater than 1.0. FIG. 1 illustrates 20% increments in deviations of hyper/ hypovolemia and/or hyper/hypoinotropy, since the volemic and inotropic deviation is more important in diagnostic and therapeutic decision-making than the abstract LCWI value.

The foregoing ellipse 14 in FIG. 1 is based upon the data obtained from normal adult patients. A similar ellipse 19 can be constructed for neonatal infants based upon a range of CI=4.2±20% liters/min/m$^2$ and a range of MAP=60±10% Torr. A line (not shown) connecting the centers of the ellipse 14 for adults and the ellipse 19 for neonates would reflect the effects of aging on hemodynamic parameters. Any of a number of additional ellipses could be constructed for any age group. For example, an ellipse (not shown) defining the empirically observed normotensive and normodynamic ranges in premature infants would be below and slightly to the right from the neonate ellipse. Ellipses for pediatric patients, depending upon their age, would appear between the ellipse. 14 for adults and the ellipse 19 for neonates.

The SVRI line 20 passing through a specific patient's point (located at the intersection of his/her MAP and CI values) represents the direction of the highest gradient of the hemodynamic response to fluid expansion/reduction and/or to inotropic therapy and provides the vectorial direction of that specific therapy. For example, volume expansion and/or positive inotropic therapy will move the patient's point along the SVRI line toward upper right in FIG. 1, whereas volume reduction and/or negative inotropic therapy will move the patient's point toward the lower left of the chart in FIG. 1.

The SVRI lines 20 on FIG. 1 also represent the arterial isocapacitance lines. Arterial capacitance is a physical description of the state of vasoactivity: hypocapacitance represents a vasoconstricted whereas hypercapacitance represents a vasodilated arterial bed. The SVRI line 20 passing through the center 16 of the normotensive/normodynamic ellipse 14 drawn on FIG. 1 (SVRI=2030 dyn.sec/cm$^5$m$^2$) represents the line of arterial normocapacitance. (A normotensive and n ormodynam is patient also exhibits arterial normocapacitance.) The LCWI line 18 passing through a specific patient's point represents the highest gradient of change of vasoactivity, hence the vectorial direction of the peripheral vasoactivity therapy. The SVRI values higher than about 2030 dyn.sec/cm$^5$m$^2$ correspond to states of arterial hypocapacitance. Such patients will require peripheral vasodilatation therapy to rectify their arterial capacitance deviation. The SVRI values lower than the arterial normocapacitance line value represent arterial hypercapacitances. The patients with these values of SVRI will require peripheral vasoconstriction to render them arterially normocapacitive. Again, the negative deviations of SVRI represent arterial hypocapacitances (vasoconstricted system), the positive deviations represent arterial hypercapacitances (vasodilated system).

From the discussion above, it is clear that volume expansion and positive inotropic therapy both have the same vectorial effect (up and to the right along the patient's SVRI line). Similarly, the volume reduction and negative inotropic therapies mask each other with the same vectorial effect (down and to the left along the patient's SVRI line). If a mean normotensive and normodynamic state (the center 16 of the ellipse 14) is the therapeutic goal, the use of volume expansion or volume reduction therapy as a single modality therapy is only appropriate on patients who happen to exhibit arterial normocapacitance (SVRI=2030 dyn.sec/cm$^5$m 2) and whose only hemodynamic abnormality is a deviation from normovolemia. A similar statement is valid for a supplemental inotropic therapy, which can be used to augment inadequate hemodynamic response to volume expansion/reduction.

Similarly, the use of a single modality peripherally vasoactive therapy can only be appropriate for a patient whose hemodynamic points happen to fall along the normovolemic and/or normoinotropic line (LCWI=4.35 kg.m/m$^2$).

However, considering statistical distribution of an infinite number of MAP and CI pairs, a vast majority of patient points will fall outside of these two specific lines related to a single modality therapy. These patients will require a complex, multi-component volemic and cardioactive drug therapy. In accordance with the invention disclosed herein, it becomes clear that the first goal of such therapy should be to correct any fluid deficiency or excess, and the second goal should be to choose proper drug therapy which will institute a normal (or selected) hemodynamic condition.

For these patients in whom single modality therapy is inappropriate, therapy should be initiated which will give rise to vectorial components on FIG. 1 parallel with each set of SVRI and LCWI lines, such that when vectorially added, will render the patient normotensive and normodynamic. Thus, the correct therapy will result in a vectorial sum of effects of volume expansion and/or reduction, together with positive and/or negative inotropic therapy and a vectorial sum of vasodilatation and/or vasoconstriction that will move the patient's point to within the ellipse 14. The specific percentage deviation from the ideal goal of therapy which can be derived from FIG. 1 will assist the clinician to quantify the titration of that specific therapeutic component.

The following two examples illustrate the efficacy of utilizing the method of the present invention in one common class of hemodynamic deviation which could benefit from correct non-invasive assessment—the treatment of essential hypertension. The examples involve two patients who were both undergoing treatment for hypertension for over one year but remained hypertensive and were both at approximately the same level of MAP though each in a different cardiodynamic state. Thus, they each required a completely different choice of therapy.

EXAMPLE 1

Male patient, 61 years old, height 173 cm, weight 78 kg, was first diagnosed hypertensive 13 years ago. He had been taking orally, once a day for the last three months, INDERIDE LA 80/50 mg (a long-acting combination of beta blockers and diuretics). The INDERIDE replaced the previous therapy which involved the use of diuretics for many years. The main reason for the change in prescription was the side effects of the simple diuretic therapy, such as cold extremities, which improved after switching to INDERIDE. The INDERIDE therapy lowered MAP into the 110 Torr level from the MAP=133 Torr level (190/105 Torr) which the patient would attain without medication. The therapy never lowered the value of his arterial pressure below MAP=110 Torr. The patient's hemodynamic and cardiodynamic state was measured with Bomed's and a sphygmomanometer. This state is shown at the point identified by reference numeral 26 in FIG. 2, which corresponds to a MAP of 110 Torr (hypertensive) and a CI of 2.6 liters/min/m$^2$ (hypodynamic). The supporting TEB measurements were TFI=29.8 ohm, IC=0.038/sec, ACI=1.05/sec$^2$, and HR=58 beat/min.

Figure 2:
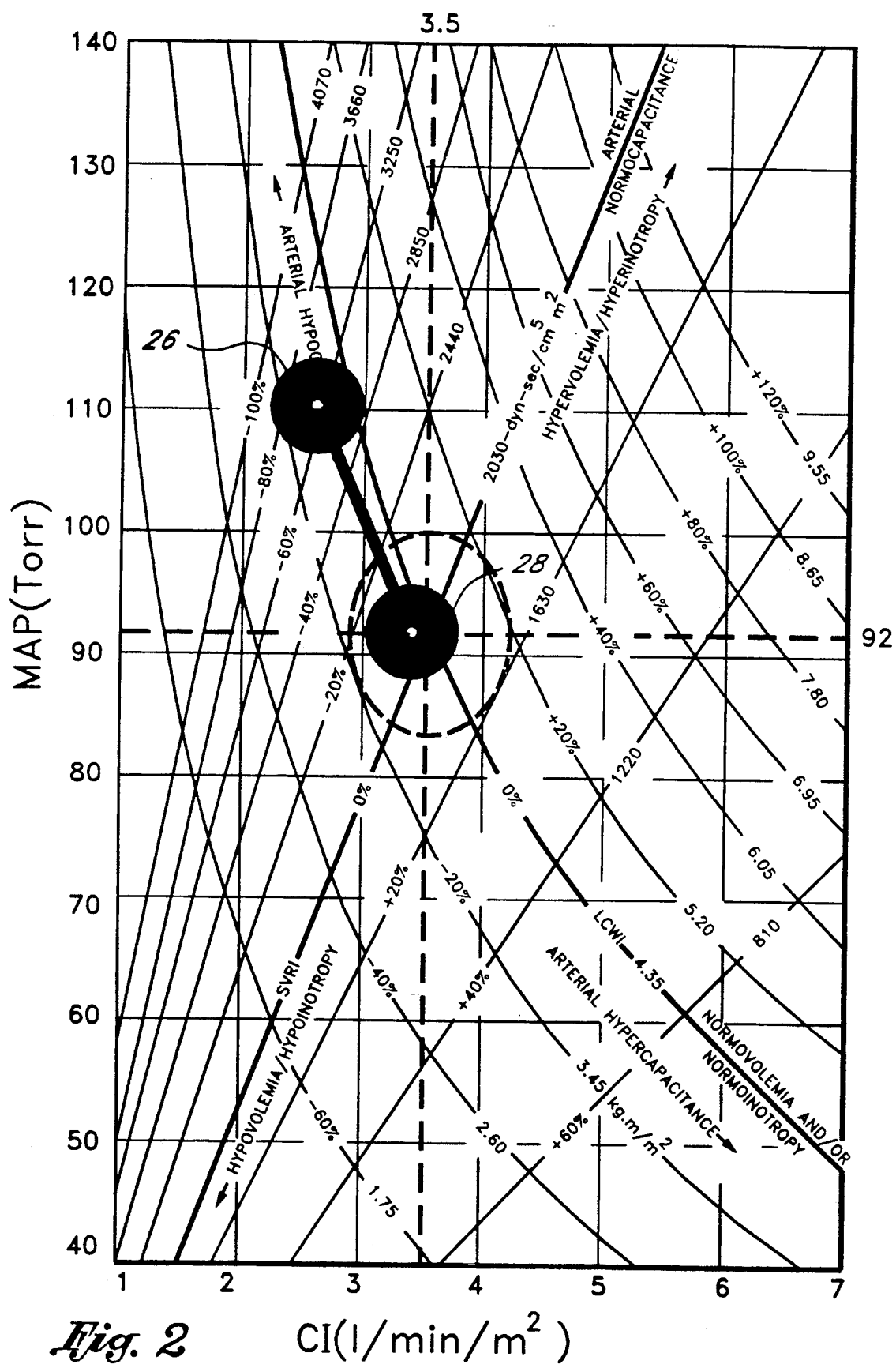
FIG. 2 illustrates the interrelationship between cardiac index, mean arterial pressure, systemic vascular resistance index and left cardiac work index in a human adult showing the changes in the parameters caused by triple modal therapy (e.g., volume reduction/negative inotropic/ vasodilation).

The physiologic interpretation of point 26 derived from FIG. 2 is relative hypovolemia and/or relative hhypoinotropy 10%, relative arterial hypocapacitance 60%. The TEB data above confirm normal inotropic state (a normal ACI value) pointing to relative hypovolemia as the contributor to the 10% deviation. However, the major 60% physiologic deviation is excessive vasoconstriction for which this patient has not been treated at all.

After the data analysis, the patient was administered 50 mg of CAPOTEN (peripheral vasodilator), and a new measurement of his hemodynamic parameters was performed six hours later (estimated half-time of CAPOTEN). This new measurement is expressed as a movement of his hemodynamic state from the initial state—point 26 to point 28 in FIG. 2. The new data relating to the patient's condition following administration of CAPOTEN are:

| | |
|---|---|
| MAP | 92 Torr (mean normotensive) |
| CI | 3.4 liters/min/m$^2$ (normodynamic) |
| TFI | 28.4 ohm |
| IC | 0.043/sec |
| ACI | 1.18/sec$^2$ |

| | |
|---|---|
| HR | 69 beats/min. |

The patient is now both normotensive and normodynamic, and has been maintained in this state by staying on the original prescription of INDERIDE LA 80/50 once a day supplemented by CAPOTEN 50 mg taken twice daily. This triple modality therapy (volume reduction/negative inotropic/ vasodilatation) is, according to analysis of the statistical distribution of patient points on FIG. 1, the most often required therapy for treatment of hypertension, though currently seldom practiced. Potential fine-tuning of the therapy in this patient could require a reduction of titration of diuretics to 25 mg/day.

EXAMPLE 2

Female patient, 44 years old, height 153 cm, weight 47 kg, treated for severe hypertension for 12 months. Most recently, she has been taking CALAN SR 240 mg (calcium channel blocker) and HYDROCHLOROTHIAZIDE 25 mg (diuretic) daily. The therapy never reduced her MAP below 110 Torr. She also complained about several side effects.

The patient's hemodynamic state was measured with the same instrumentation as in Case 1. Her hemodynamic state is expressed as point 30 in FIG. 3:

| | |
|---|---|
| MAP | 120 Torr |
| CI | 4.9 liters/min/m$^2$ |
| TFI | 24.4 ohm |
| IC | 0.081/sec |
| ACI | 2.28/sec$^2$ |
| HR | 73 beats/min |

Figure 3:
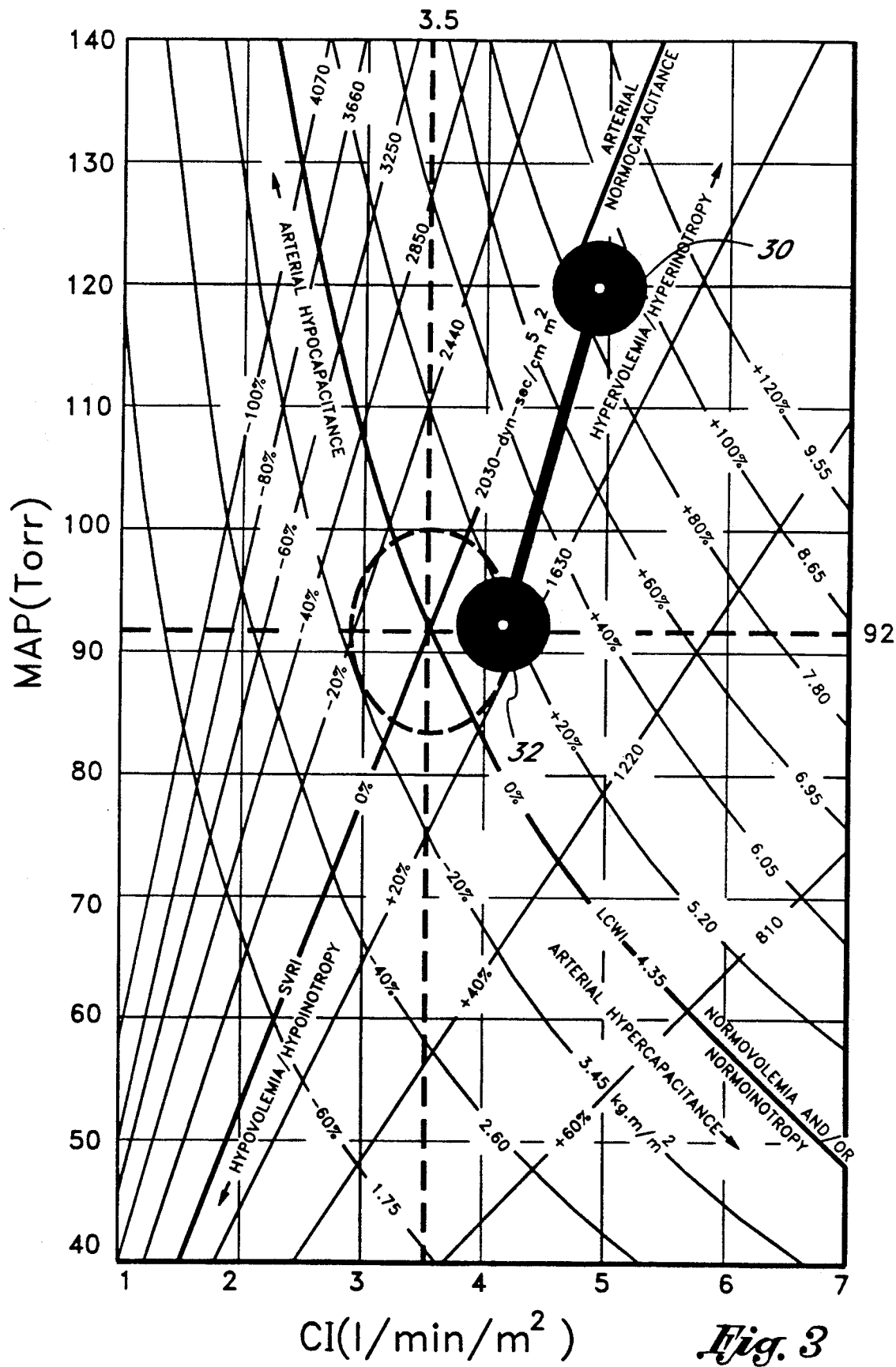
FIG. 3 illustrates the interrelationship between cardiac index, mean arterial pressure, systemic vascular resistance index and left cardiac work index in a human adult showing the changes in the parameters caused by triple modal therapy including the stronger utilization of negative inotropes in conjunction with lowering the heart rate, supplemented by volume reduction.

The position of point 30 in FIG. 3 shows a 15% deviation toward arterial hypercapacitance and 90% toward hypervolemia and/or hyperinotropy. The supporting TEB data above document that (a) the patient is hyperdynamic (CI and SI values much higher than their normal range), (b) hypervolemic (TFI value is significantly below normal range for females indicating an excess of fluids), and (c) hyperinotropic (ACI and IC values higher than their normal range). The 90% increase of LCWI also demonstrates a potential long-term problem of the patient's condition—excessive work of the pump (excessive myocardial consumption). In the absence of the knowledge that the patient is hyperdynamic, she could never have been treated correctly.

Analysis of the data corresponding to point 30 on FIG. 3 clearly points toward a therapy which should include (a) stronger utilization of negative inotropes in conjunction with (b) decreasing capacitance, supplemented by (c) volume reduction.

The patient was administered INDERIDE LA 80/50 mg. The patient's parameters were then measured again after 24 hours. The new hemodynamic data are expressed as movement of the patient's hemodynamic point from the point 30 to point 32 in FIG. 3. The patient's data corresponding to point 32 were:

| | |
|---|---|
| MAP | 93 Torr (normotension) |
| CI | 4.1 liters/min/m$^2$ |
| TFI | 28.6 ohm (now within normal range) |
| IC | 0.071/sec |
| ACI | 1.86/sec$^2$ |

| | |
|---|---|
| HR: | 58 beats/min |

The patient began taking INDERIDE LA 80/50 mg once a day and was maintained normotensive and normodynamic. However, during twice-daily blood pressure measurements, it was noted that 12 hours after taking the drug, her MAP decreased to a value of MAP=90 Torr, while 24 hours later (at the time of taking another dose), it was consistently at a value of MAP=98 Torr. She was metabolizing the drug at a faster rate, causing larger periodic variation of the drug level in her system. To prevent such a hemodynamic variation, the prescription was split and skewed by 12 hours. INDERAL LA 80 mg is now taken once a day and the diuretic (50 mg) taken also once a day, though 12 hours later. The patient's MAP is maintained this way at 93 Torr level, and the patient is hemodynamically stable without the side effects reported on the initiation of this study.

The preceding case studies illustrate the proper measurement and identification of a patient's hemodynamic and physiologic state in accordance with the method of the present invention. This can be easily accomplished and the deviation from the ideal state clearly defined. The patient can be treated so as to achieve an ideal (or selected) hemodynamic state in real time. Significantly, the important results of the described method are obtainable based upon non-invasive physiologic and hemodynamic measurements.

Description of An Exemplary Electronic System for Implementing the Method of the Present Invention FIG. 4 is a schematic representation of an exemplary electronic system for implementing the method of the present invention. As illustrated, a patient 100 is electrically connected to an electrical bioimpedance monitor (EBM) 104, which, preferably, is an NCCOM ® 3-R7 non-invasive continuous cardiac output monitor manufactured by BoMed Medical Manufacturing Ltd. of Irvine, California. The electrical bioimpedance monitor 104 is connected to the patient 100 via a first electrical conductor 110 connected to a first connector 111, a second electrical conductor 12 connected to a second connector 113, a third electrical conductor 114 connected to a third connector 115, and a third electrical conductor 116 connected to a fourth connector 117. The first electrical conductor 110 is connected to a first pair of electrodes 120a and 120b that are positioned on the neck of the patient 100 at the intersection of a line encircling the root of the neck with the frontal plane of the patient 100 (the frontal plane is an imaginary plane dividing the anterior and posterior sections of the neck and shoulder of the patient 100). Thus, the two electrodes 120a and 120b are positioned approximately 180 apart around the circumference of the neck. The second electrical conductor 112 is connected to a second pair of electrodes 122a and 122b that are positioned on the patient's neck approximately 5 centimeters directly above the first pair of electrodes 120a and 120b. The third electrical conductor 114 is connected to a third pair of electrodes 124a and 124b that are positioned on the patient's thorax along the mid-axillary line at the xiphoid process level with the electrode 124a positioned approximately 180° apart from the electrode 124b. The fourth electrical conductor 116 is electrically connected to a fourth pair of electrodes 126a and 126b that are positioned on the patient's thorax approximately 5 centimeters directly below the third pair of electrodes 124a and 124b. It should be understood that the positioning of the electrodes can be varied to accommodate bandages and other obstructions so long as the electrodes in each pair of electrodes are approximately 180° apart. Other electrode combinations (e.g., band electrodes, and the like) can also be used.

The electrical bioimpedance monitor 104 includes a serial data output connector 130 which is electrically connected via a serial data line 132 to a computer 140, such as an IBM ®PC, XT, AT, or the like. Other computers can also be advantageously used. The computer 140 is connected to a keyboard 142 and to a monitor 144 that operate in known conventional manners. Preferably, the computer 140 is also connected to a printer 146. The computer 140 receives serial data from the electrical bioimpedance monitor 104, processes the data and displays the processed data on the monitor and the printer. The details of the data received from the electrical bioimpedance monitor 104 and the processing functions of the computer 140 will be discussed in additional detail below. It should be understood that a parallel data connection can also be used between the electrical bioimpedance monitor 104 and the computer 140 in alternative embodiments of the invention.

The electrical bioimpedance monitor 104 further includes a set of electrical output connectors 150 that provide an ECG compatible output signal thereon. The ECG compatible output signal is connectable to a conventional ECG monitoring device 152 via an ECG cable 154. As will be discussed below, the ECG compatible output signal is selectably representative of the electrical activity of the patient's heart or the electrical bioimpedance measurements.

The electrical bioimpedance monitor 104 preferably further includes an ECG input connector 160 that is connectable to a set of conventional ECG electrodes (not shown) on the patient 100 via a set of ECG input lines 162

The electrical bioimpedance monitor 104 operates in a known manner to derive significant cardiac information from the electrical bioimpedance changes that occur during each cardiac cycle. Briefly, the electrical bioimpedance monitor 104 operates by generating a high frequency, substantially constant current that is provided as an output from the connectors 113 and 117 (labeled as CIO to represent the current injection outputs). The constant current is coupled to the patient via the second conductor 112 and the fourth conductor 116 and is injected into the body of the patient 100 between the second pair of electrodes 122a and 122b and the fourth pair of electrodes 126a and 126b so that the current flows through the patient's thorax between the two pairs of electrodes. The constant current causes a voltage to be induced in the patient's thorax that is proportional to the electrical impedance of the thorax. The induced voltage is sensed between the first pair of electrodes 120a and 120b and the third pair of electrodes 126a and 126b. The sensed voltage is conducted to the electrical bioimpedance monitor 104 via the first conductor 110 and the third conductor 114 and is provided as an input to the electrical bioimpedance monitor 104 via the connectors 111 and 115 (labeled as SVI to represent the sensed voltage input). The electrical bioimpedance monitor 104 converts the sensed voltage into a representation of the electrical bioimpedance of the thorax. The electrical bioimpedance as a function of time is referred to as $Z(t)$. The representation of the electrical bioimpedance is available as an output on a connector 162. The electrical impedance of the thorax depends upon a number of factors, one of which is the quantity of blood in the vasculature system of the thorax which changes throughout each cardiac cycle. The electrical impedance changes caused by the blood in the thorax are time-varying and can be detected by differentiating the detected sensed voltage to provide a representation of the differentiated electrical bioimpedance (i.e., $dZ/dt$) which includes both changes caused by blood flow in the thorax and changes caused by respiration and other more slowly changing factors.

The NCCOM ® 3R7 processes the differentiated bioimpedance information and provides a processed signal that represents the electrical bioimpedance changes ($dZ/dt$) caused by blood flow. The processed $dZ/dt$ signal is selectably provided as an output signal from the electrical bioimpedance monitor 104 on a $dZ/dt$ output connector 164 so that the $dZ/dt$ signal can be provided as an input to an oscilloscope (not shown) or other suitable equipment for monitoring the $dZ/dt$ signal.

The electrical bioimpedance monitor 104 can also derive an ECG signal from voltages present on the four input lines 110, 112, 114 and 116. The ECG signal which represents the electrical activity of the patient's heart can also be sensed by the four pairs of electrodes described above. The ECG signals can be separated from the sensed voltage proportional to the electrical bioimpedance since the injected constant current signal is a relatively high frequency (e.g., 50–100 kHz) and the ECG signals generated by the heart have a considerably lower frequency content. Thus, suitable filters can be used to separate the two signals. Alternatively, in the event that a suitable ECG signal cannot be derived from the electrical input signals on the four lines 110, 112, 114 and 116, the ECG input connector 160 can be connected to suitably positioned electrodes (not shown) to obtain an ECG input signal. The ECG signal derived from the four input lines 110, 112, 114, and 116, or the ECG signal derived from a separate ECG signal on the ECG input connector 160 is selectably output as an ECG compatible output signal on the set of ECG output connectors 150 that can be recorded and displayed on the ECG monitoring device 152. The preferred embodiment of the electrical bioimpedance monitor 104 (e.g., the NCCOM ® 3-R7) preferably includes a switch (not shown) to switch the output signal on the set of ECG output connectors 150 from the ECG signal to a signal representative of the processed $dZ/dt$ signal. For example, in the preferred embodiment, the output signal has a magnitude of 1 millivolt for each ohm per second of change in the electrical bioimpedance. A signal of this magnitude is compatible with the range of input voltages that can be provided as inputs to a conventional ECG monitor.

The electrical bioimpedance monitor 104 further processes the differentiated electrical bioimpedance information and the ECG information and calculate additional cardiovascular system information that is derived from the differentiated electrical bioimpedance information and the ECG. In particular, the electrical bioimpedance monitor 104 calculates the pre-ejection period (PEP), which is measured between the onset of Q of the QRS complex of the ECG signal to the opening of the aortic valve), and the ventricular ejection time (VET), which is measured between the opening and the closing of the aortic valve. The ventricular ejection time is a direct measure of the duration of the mechanical systole of the patient's heart. From these two calculated parameters, the electrical bioimpedance monitor 104 calculates the systolic time ratio (STR) as follows:

$$STR = PEP/VET \quad (4)$$

The calculated systolic time ratio is displayed and is provided as an output parameter from the electrical bioimpedance monitor 104.

The electrical bioimpedance monitor 104 derives the heart rate period (HRP) from the ECG signal. The heart rate (HR) is derived from the heart rate period in a known manner (e.g., HR=60/HRP). In addition, the heart rate period can be used in combination with the ventricular ejection time (VET) to calculate the ejection ratio (ER) as follows:

$$ER(\%) = (100 \times VET)/HRP \quad (5)$$

The electrical bioimpedance monitor 104 further calculates the thoracic fluid index (TFI) which is a value that represents the total resistance of the thorax to the flow of the high frequency, constant current injected into the thorax as measured by the electrical bioimpedance monitor 104. Typical values for the thoracic fluid index vary from 20-33 ohms for male adults and 27-48 ohms for female adults and children.

The electrical bioimpedance monitor 104 calculates the ejection velocity index (EVI) which is the maximum value of the rate of change of thoracic impedance change (i.e., $EVI = (dZ/dt)_{max}$) during the systolic upstroke. The ejection velocity index corresponds to the peak ejection velocity and the peak flow in the descending thoracic aorta, and is directly related to the heart's contractility when it is normalized by the thoracic fluid index. The peak ejection velocity is measured in centimeters per second and the peak flow is measured in milliliters per second. The ejection velocity index represents these two parameters in ohms per second. Because of the variability of the thoracic fluid index during a long range therapeutic procedure, the ejection velocity index alone is generally not usable to assess changes in a patient's inotropic state. Thus, the exemplary electrical bioimpedance monitor 104 (i.e., the NCCOM® 3-R7) calculates the index of contractility (IC) as the ratio of the ejection velocity index to the thoracic fluid index (i.e., IC=EVI/TFI). The index of contractility is displayed and is provided as an output parameter from the electrical bioimpedance monitor 104.

The electrical bioimpedance monitor 104 calculates, displays and provides as an output signal on the serial data line 132 a digital output signal that represents the stroke volume (SV) of the patient's heart. The stroke volume is calculated from the above-described parameters as follows:

$$SV = VEPT \times VET \times (EVI/TFI) = VEPT \times VET \times IC \quad (6)$$

where VEPT is the physical volume of the electrically participating tissue in the thorax in milliliters. The parameter VEPT is calculated as $VEPT = (L^3/4.25)$, where L is the equivalent thoracic length in centimeters that is derived from the patient's height and body weight which are entered as input parameters by the clinician. Since stroke volume is a function of body mass, in most diagnostic and therapeutic procedures a normalized stroke index (SI) is desirable. The stroke index is determined by dividing the stroke volume by the patient's body surface area, calculated from the patient's height and weight, to obtain the stroke index normalized by body surface area, or by dividing the stroke volume by the patient's weight to obtain the stroke index normalized by weight.

The electrical bioimpedance monitor 104 calculates, displays and provides as a digital output signal the cardiac output (CO) in liters per minute. The cardiac output is calculated from the stroke volume and the heart rate as follows:

$$CO = SV \times HR \quad (7)$$

Cardiac output expresses the perfusion capability of the patient's heart. The resting cardiac output of a patient is a function of the patient's body mass. In order to be able to compare the adequacy of oxygen delivery of individuals of different body masses, the cardiac output is preferably normalized by body surface area or body weight to obtain the cardiac index (CI). The cardiac index by body surface area ($CI_{BSA}$) is obtained by dividing the cardiac output by the calculated body surface area derived from the height and weight parameters input by the clinician. The cardiac index by weight ($CI_{weight}$) is calculated by dividing the cardiac output by the patient's weight. The electrical bioimpedance monitor 104 selectably provides either the cardiac output or one of the two cardiac indices as a display and output parameter.

Another parameter that is calculated, displayed and provided as an output is the peak flow (PF) which is calculated from the thoracic volume VEPT and the index of contractility IC as follows:

$$PF = VEPT \times IC \times CONSTANT \quad (8)$$

where CONSTANT is a dimensionless constant that is derived empirically. For example, in exemplary adult patients the constant is approximately 2.0. Peak flow represents the highest rate of left-ventricular volumetric delivery during the ejection phase of the cardiac cycle in milliliters per second. Peak flow is linked directly to the ejection phase contractility of the heart and as such is dependent on volemic status. Peak flow is one parameter that describes left ventricular performance. Alternatively, the electrical bioimpedance monitor 104 calculates, displays and outputs the peak flow index (PFI) which is the peak flow normalized by body surface area or body weight, depending upon which of the two indexing systems is selected.

The electrical bioimpedance monitor 104 also calculates, displays and provides as a digital output signal the ejection fraction (EF) which is calculated from the ratio of the pre-ejection period PEP to the ventricular ejection time VET. The ejection fraction is typically expressed as a percentage. The calculation is performed internally to the electrical bioimpedance monitor 104 in accordance with the following equation:

$$EF = 0.84 - (0.64 \times (PEP/VET)) \quad (9)$$

where the two constants have been derived empirically The ejection fraction represents the volumetric emptying efficiency of the left ventricle, and thus represents the percentage of total volume contained in the ventricle just before the beginning of the systolic phase.

The electrical bioimpedance monitor 104 further calculates, displays and outputs the end-diastolic volume (EDV) which is volume of blood remaining in the heart at the end of the diastolic portion of the cardiac cycle and is calculated as the stroke volume divided by the ejection fraction. In other words:

$$EDV = SV/EF \tag{10}$$

where EDV is in milliliters. The end-diastolic volume is preferably indexed by body surface area or body weight for comparison between patients. The indexed end-diastolic volume is referred to as the end-diastolic index (EDI) and is calculated as:

$$EDI_{BSA} = EDV/BSA \tag{11a}$$

$$EDI_{WEIGHT} = EDV/WEIGHT \tag{11b}$$

where $EDI_{BSA}$ is in milliliters per square meter, and where $EDI_{weight}$ is in milliliters per kilogram.

The inotropic state of the left ventricle of the patient's heart (i.e., its contractile state), represented by the index of contractility (IC), is dependent upon the fluid volume, the preload of the heart and the afterload of the heart. In contrast, the initial acceleration of the from the left ventricle of the heart takes place in the first 10–20 milliseconds after the aortic valve opens and is related to the left ventricular impulse. The initial acceleration is substantially less load dependent and is thus more closely defines the inotropic state of the patient's vasculature system. As discussed above, the dZ/dt signal in ohms per second is processed by the electrical bioimpedance monitor 104 as an ohmic image of blood flow (milliliters per second) and blood velocity (centimeters per second). The maximum rate of change of dZ/dt (i.e., $d^2Z/dt^2_{max}$) represents the ohmic counterpart of the acceleration of the blood. This parameter divided by the thoracic fluid index (TFI) is calculated and displayed as the acceleration index (ACI). In other words, $ACI = d2Z/dt^2_{max}/TFI$. The acceleration index is also provided as a serial data output parameter on the serial data line 130.

The electrical bioimpedance monitor 104 of the preferred embodiment of the apparatus of the present invention calculates the foregoing parameters and displays selected ones of the parameters on a display panel (not shown) that is included as part of the electrical bioimpedance monitor 104. Furthermore, the calculated parameters are provided as serial output signals on the serial output connector 130 and thus as inputs to the computer 140 via the serial data line 132. In the exemplary electrical bioimpedance monitor 104 described herein (i.e., the NCCOM ® 3-R7), the output signals on the serial output connector 130 are provided in conventional RS-232 format at 9600 baud. Preferably, the output data format is as illustrated in FIG. 5, with each character of data comprising a start bit, seven data bits, a parity bit (set to provide even parity in the preferred embodiment), and two stop bits. Other suitable formats can be used. It should be understood that the preferred format for the transmitted data is the standard ASCII codes for the numeric characters and the punctuation.

In the preferred embodiment incorporating the NCCOM ® 3-R7, the parameters can be provided as output signals in at least two different formats referred to as the FAST mode and the SLOW mode. In the slow mode, the electrical bioimpedance monitor 104 transmits eleven of the parameters described above in sequence, a character at a time, and outputs the calculated parameters on the serial data line 132 once for every sixteen heart beats. The electrical bioimpedance monitor 104 preferably outputs the average values of the parameters over the sixteen heartbeats. For example, in one exemplary embodiment, the following format for the transmission of the SLOW mode parameters is used:

:CO SV EDV PF EF HR TFI IC ER STR ACI
 HOUR:MIN where the first eleven parameters are defined as discussed above, and HOUR and MIN are the twenty-four hour time of day entered into the electrical bioimpedance monitor 104 and updated in accordance with a real-time clock within the electrical bioimpedance monitor 104. Preferably, the hour and minute information is transmitted only once every minute rather than every transmission. The first colon in the transmission is used to indicate the beginning of a transmission sequence. Other delimiters could of course be used. The first colon can be distinguished from the colon between the hour and minute portion of the time portion as being preceded by a space rather than a number. Thus, the computer 140 can readily use the first colon to synchronize with the serial data from the electrical bioimpedance monitor 104. Preferably, the data is output from the electrical bioimpedance monitor 104 as a series of digits only. The dimensions and the expected ranges are known by the software algorithms in the computer 140. It should be understood that the transmitted data comprises numeric data, which may include a decimal point, separated by blank spaces (hexadecimal 20), and delimited by the colons.

Alternatively, the SLOW mode parameters are output as follows:

:CI SI EDI PFI EF HR TFI IC ER STR ACI
 HOUR:MIN wherein the cardiac index (CI), the stroke index (SI), the end-diastolic index (EDI) and the peak flow index (PFI) are substituted for their respective unindexed values. The indexing can be in accordance with body surface area or weight, as discussed above.

Preferably, additional patient information, such as the patient's sex, identification number, height, weight, VEPT (thoracic volume), and calculated body surface area (BSA), are also transmitted from the electrical bioimpedance monitor 104 to the computer 140. Preferably, the additional patient information is transmitted only once at the beginning of the data transmission as these parameters should not change for a patient during a diagnostic session.

In the FAST mode, the calculated parameters are transmitted once for each heart beat. Because of the transmission rates and the time required to perform the calculations, in the FAST mode, only six of the foregoing parameters are transmitted. For example, the following exemplary format is used for unindexed parameters:

: CO SV EDV PF EF HR HOUR:MIN

Alternatively, the indexed parameters can be transmitted as follows:

: CI SI EDI PFI EF HR HOUR:MIN

As with the SLOW mode, the hour and minute information is preferably transmitted only once per minute rather than in every transmission. Furthermore, the other patient parameters and identification information, discussed above, are preferably transmitted once at the beginning of diagnostic session.

Additional information regarding the operation of the exemplary NCCOM® 3-R7 electrical bioimpedance monitor in sensing the electrical bioimpedance changes and calculating the above-described parameters can be found in "NCCOM®3-R7 CARDIOVASCULAR MONITOR OPERATOR'S MANUAL," available from BoMed® Medical Manufacturing Ltd., 5 Wrigley Street, Irvine, Calif. 92718.

One additional input to the computer 140 is required in order to complete the system of the present invention. As discussed above, the mean arterial blood pressure (MAP) is a factor in the determination of the appropriate therapeutic procedure to return the patient to a normal range of conditions for the patient's vasculature system. The mean arterial blood pressure can be provided as an input by a number of different methods. One of the simplest and most straight forward apparatus and methods for inputting the mean arterial blood pressure to the computer 140 is to measure the mean arterial blood pressure using a conventional occlusive cuff to determine the systolic and diastolic pressures, calculating the mean arterial blood pressure in accordance with the Equation 1, above as:

$$MAP = \frac{SYSTOLIC - DIASTOLIC^1}{3} + DIASTOLIC \quad (1)$$

The result of the calculation is then entered into the computer 140 using the keyboard 142. This combination of apparatus and method has the disadvantage of requiring manual input from a clinician with the accompanying possibility of introducing error into the computer 140. Furthermore, this combination of method and apparatus does not lend itself to automatic monitoring of the condition of the patient's vasculature system. Thus, it is preferable that an automated system be used for measuring the patient's mean arterial blood pressure and providing it as an input to the computer 140.

Figure 6:
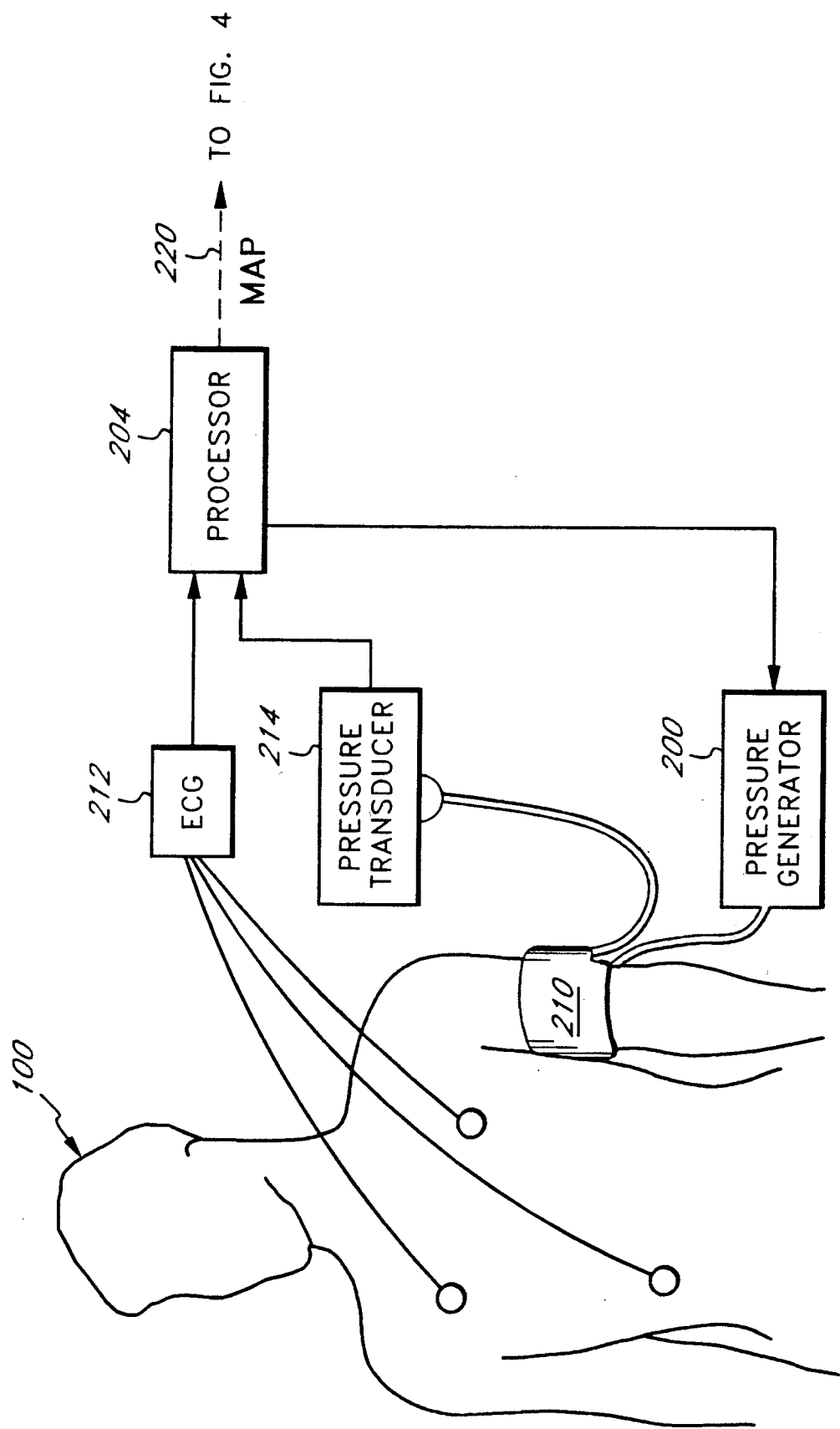
FIG. 6 illustrates an exemplary system of the present invention that includes an automatic pressure measuring system.

A number of systems are available for automatically measuring a patient's blood pressure and providing it as an input to the computer 140. One such system is described in U.S. Pat. No. 4,677,984, which is incorporated herein in its entirety. The system disclosed in U.S. Pat. No. 4,677,984 is illustrated in simplified form in FIG. 6. As illustrated, the system includes an automatic cuff pressure generator 200 controlled by a processor 204. The pressure is selectively coupled to an occlusive cuff 210. The system further includes an ECG monitoring device 212 to sense the occurrence of an R-wave in the ECG signal of the patient. The system includes a pressure transducer 214 detects transitions in the pressure in the occlusive cuff 210 caused by the passage of a bolus of blood beneath the cuff 210 when the arterial pressure exceeds the cuff pressure during a cardiac cycle. The transitions are timed with respect to the occurrence of the R-wave of the ECG to maintain a record of the pressure transitions as the pressure on the occluding bladder is systematically decreased or increased. The recorded pressure transitions and times are used to reproduce the arterial blood pressure waveform from which the mean arterial blood pressure can be calculated. In the present invention, the processor 204 of FIG. 6 provides an output signal representing the mean arterial blood pressure that is provided as an input signal to the computer 140 of FIG. 4. This connection is shown as a dashed line 220 in FIGS. 6 and 4. In a fully integrated system, the computer 204 used to record the pressure transitions and times advantageously can be the same computer 140 that receives the serial data information from the electrical bioimpedance monitor 104.

Figure 7:
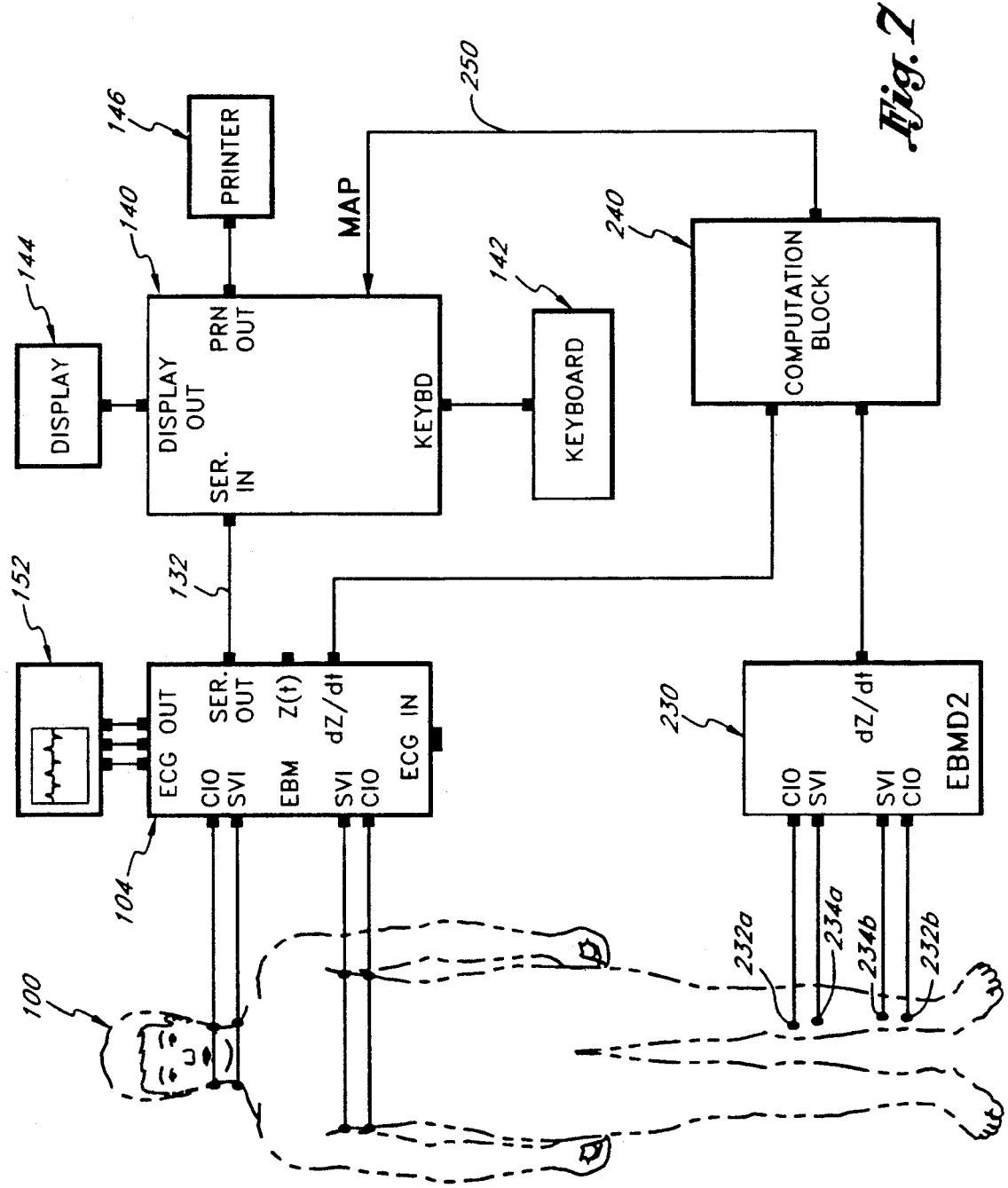
FIG. 7 illustrates an exemplary system of the present invention that includes an alternative automatic pressure measuring system that utilizes electrical bioimpedance techniques.

The pressure can also be measured using electrical bioimpedance techniques as set forth in allowed U.S. Pat. application Ser. No. 111,699, filed on Oct. 21, 1987, and assigned to the assignee of this application, and which is incorporated herein by reference. This system is illustrated in part in FIG. 7. As illustrated in FIG. 7, the automatic blood pressure measuring system includes a pair of electrical bioimpedance measuring devices, one of which is the electrical bioimpedance monitor 104, disclosed and described above. A second electrical bioimpedance measuring device (EBMD2) 230 is connected to a set of current injecting electrodes 232a and 232b and a set of current sensing electrodes 234a and 234b on the calf of the patient's leg that defines a second body segment for bioimpedance sensing. The second electrical bioimpedance bioimpedance monitor 104, as it is only necessary to detect the peak on the change in the electrical bioimpedance in the patient's leg. As described in U.S. Pat. application Ser. No. 111,699, a computation circuit 240 receives the dZ/dt output signals from the electrical bioimpedance monitor 104 and the electrical bioimpedance measuring device 230 and calculates the time delay (i.e., the arterial pulse propagation delay) between the peaks in the two dZ/dt signals. The computation circuit 240 uses the measured time delay to determine the mean arterial blood pressure therefrom. As set forth in U.S. Pat. application Ser. No. 111,699, the time delay and the spacing of the second body segment of the leg from the first body segment of the patient's thorax provide sufficient information from which the mean arterial blood pressure (MAP) can be calculated. The computation block 240 advantageously provides the calculated mean arterial blood pressure as an output on a line 250 which is connected to an input to the computer 140. Thus, the mean arterial blood pressure is provided as an input to the computer 140. It should be understood that the computation block 240 can advantageously be a microprocessor or other programmable computation device. Although shown as a single serial data line 250, it should be understood that the data can be transmitted from the computation block 240 to the computer 140 via a parallel data bus, for example.

Other known automatic or manual methods and apparatus can be used to measure the mean arterial blood pressure and provide it as an input to the computer 140 for use in calculating the therapeutic information, as will be described hereinafter.

The computer 140 uses the data information from the electrical bioimpedance monitor 104 and the mean arterial blood pressure provided as a data input from the keyboard 142 or from the automated system of FIG. 6 or FIG. 7. An exemplary flow chart for the operation of the computer 140 is illustrated in FIG. 8.

Description of the Flow Chart of the Computer Algorithms

Figure 8:
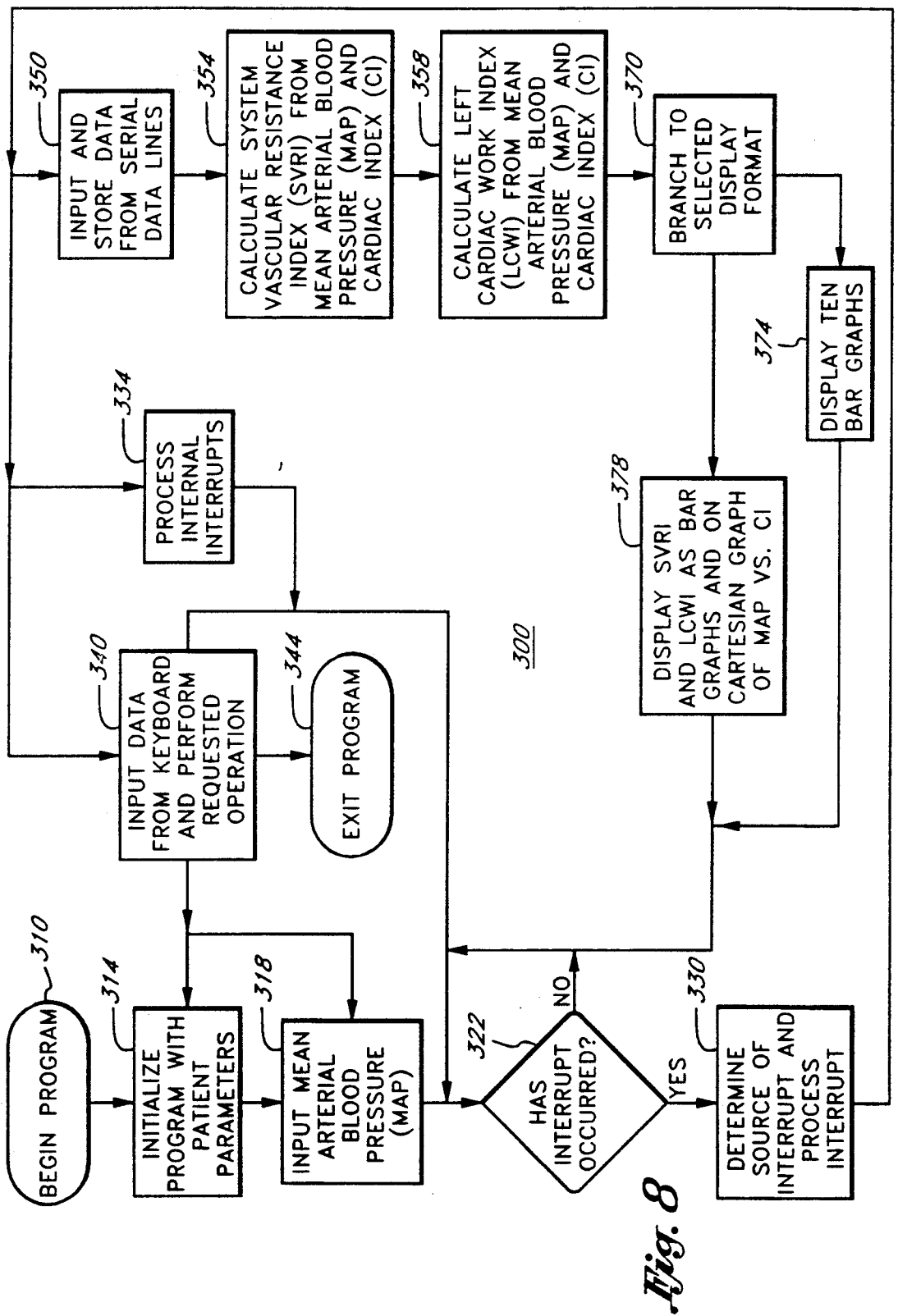
FIG. 8 is a flow chart of an exemplary computer program algorithm for implementing the present invention

As illustrated in FIG. 8, the computer 140 is programmed with an algorithm 300 that includes an entry block 310 wherein the program begins. Thereafter, the algorithm enters a first activity block 314 in which the program is initialized. The program requests various parameters from the clinician including the patient's name and other identification information. Thereafter, the algorithm enters a second activity block 318 in which the computer inputs data that represents the mean arterial blood pressure (MAP). The MAP data can be entered from the keyboard 142 when the MAP is provided by manual methods and apparatus. Alternatively, the MAP can be provided as a direct digital input from the automated blood pressure measuring system of FIG. 6 or the automated blood pressure measuring system of FIG. 7, as discussed above. After entering and storing the MAP, the computer algorithm enters a decision block 322 wherein the algorithm monitors waits for an interrupt indicating that new data has begun to arrive on the serial data input lines from the electrical bioimpedance monitor 104, that the clinician has entered a command from the keyboard 142, or that other real-time activities have occurred that must be handled, such as the clock interrupt internal to the computer 140. So long as no interrupt has occurred, the algorithm will reenter the decision block 322.

When an interrupt occurs, the algorithm will enter a process block 330 wherein it processes the interrupt and branches to the appropriate routine determined by the nature of the interrupt. The various routines are shown as three generalized routines. If the interrupt is an internal computer interrupt, such as the real-time clock interrupt, the algorithm enters an activity block 334 wherein the internal computer interrupts are processed in known conventional manners. These interrupts are handled in a conventional manner by the disk operating system (DOS) or other system level programs provided with the computer 140. Thus, the handling of these interrupts is transparent to the algorithm itself and control is returned from the activity block 334 back to the decision block 322 where the algorithm awaits the next interrupt.

If the interrupt is a keyboard entry interrupt, the algorithm enters an activity block 340 wherein the data entered via the keyboard 142 is provided as an input to the algorithm for further processing. For example, the data can indicate that the clinician desires to re-initialize the algorithm. Thus, a path is illustrated that returns the algorithm control back to the first activity block 314 wherein the algorithm is re-initialized. The data can also indicate an update of the patient's mean arterial blood pressure. Thus, a path is illustrated from the activity block 340 to the second activity block 318 wherein the MAP is updated. It should be understood that in the embodiment of FIG. 6 or the embodiment of FIG. 7, wherein the MAP is generated automatically, an interrupt from the external computer 210 (FIG. 6) or the computer 220 (FIG. 7) causes the computer 140 to input the MAP data from the corresponding external computer.

The keyboard entry can also be a request to terminate the program. Thus, a path is provided from the keyboard entry activity block 340 to a program termination block 344. Other keyboard entries could of course envisioned. However, rather than attempt to enumerate all possible entries, a path is illustrated from the keyboard entry activity block 340 back po the decision block 322 wherein the algorithm waits for the next interrupt.

The third general type of interrupt is generated when serial data inputs are received from the electrical bioimpedance monitor 104. As set forth above, the electrical bioimpedance monitor 104 periodically outputs the calculated parameters of the vasculature system to the computer 140. When the serial data is received by the computer 140, an interrupt is generated and the algorithm enters an activity block 350 wherein the computer inputs the data from the electrical bioimpedance monitor 104. Thereafter, the algorithm enters an activity block 354 wherein the computer 140 calculates the systemic vascular resistance index (SVRI) in accordance with the Equation (2) as follows:

$$SVRI = \frac{(MAP - CVP) \times 80}{CI} \qquad (2)$$

As discussed above, CVP is the central venous pressure which is estimated to be approximately 3 Torr. The cardiac index (CI) is one of the parameters received on the serial data line 132 from the electrical bioimpedance monitor 104. The dimensions of SVRI resulting from the above calculation is in dyn.secm 5m$^2$, also referred to herein as fluidic ohms per square meter (F.Ohms/m$^2$).

After calculating the SVRI, the algorithm enters an activity block 358 wherein the computer 140 calculates the left cardiac work index (LCWI) in accordance with Equation (3) as follows:

$$LCWI = (MAP - PAOP) \times CI \times 0.0144 \text{ kg.m/m}^2 \qquad (3)$$

As discussed above, PAOP is pulmonary artery occluded pressure in Torr, CI is the cardiac index in liters/min/m$^2$, and 0.0144 is a constant of proportionality. As further discussed above, in the typical patient, the PAOP will be approximately 6 Torr, and this value may be ordinarily assumed without subjecting the data to any significant error. However, a patient's actual PAOP can vary sufficiently to justify determination of the actual PAOP value for use in Equation (3) under conditions of pump failure. In such a case, the actual PAOP is entered via the keyboard 142 by the clinician. The dimensions of LCWI resulting from the above calculation are in kilograms per square meter (kg.m/m$^2$).

Figure 10:
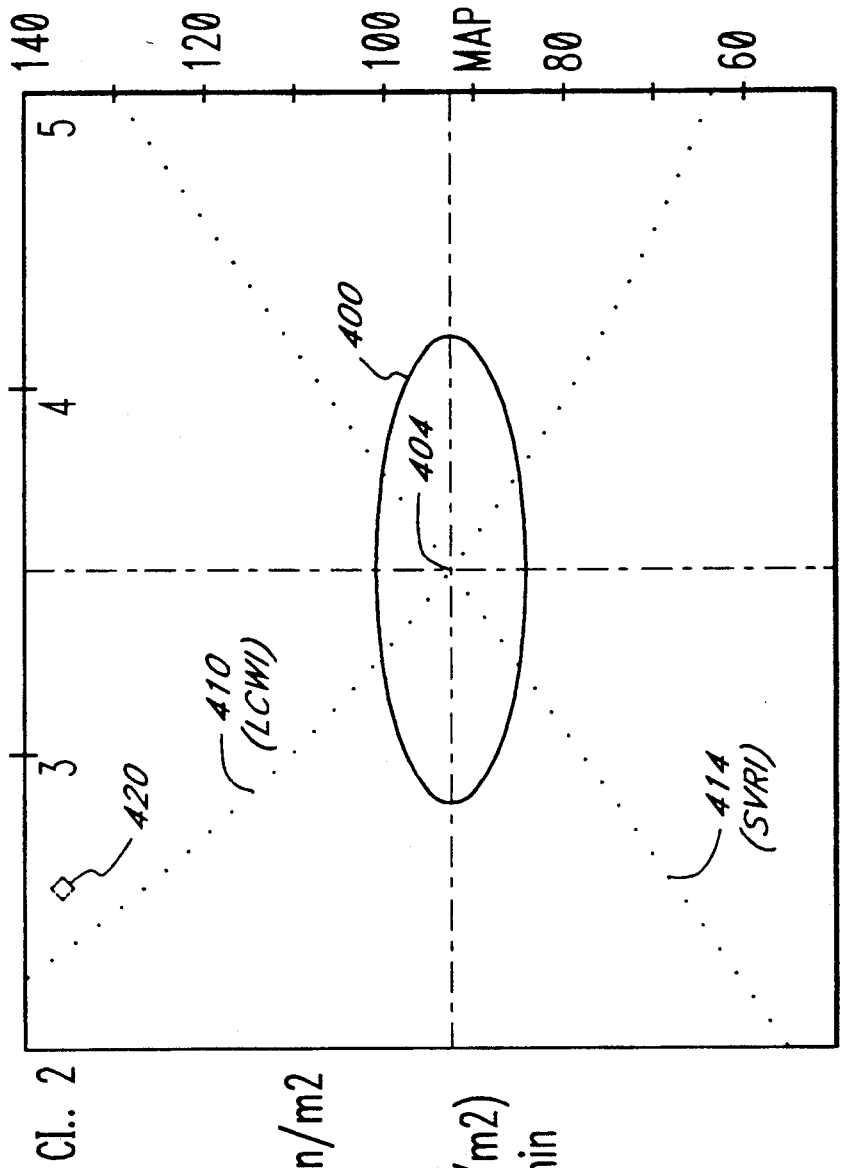
FIG. 10 illustrates an alternative screen display that utilizes cartesian graphs to display the hemodynamic status and the percentage deviation from a selected goal of a patient's cardiovascular system.

After calculating the left cardiac work index, the algorithm enters an activity block 370 wherein the computer 140 branches to a selected one of an activity block 374 or an activity block 378 wherein the computer provides a visual display of the calculated data. Two primary alternative data displays are advantageously provided in the preferred embodiment of the present invention. The selection of which type of display to provide is one of the selections that can be entered via the keyboard when the computer 140 is in the activity block 340. Other types of displays can also be advantageously provided. After providing an updated display as an output in either the activity block 374 or the activity block 378, the algorithm returns to the decision block 322 to await the next interrupt. Additional details regarding the two primary types of displays generated in accordance with the present invention are illustrated in FIGS. 9 and 10, and are described hereinafter.

One of the two primary displays is provided when the computer enters the activity block 374. The display associated with the activity block 374 is illustrated in FIG. 9. In FIG. 9, the cardiovascular and hemodynamic data are displayed as a bar chart comprising a series of ten bar graphs. The bar chart of FIG. 9 is referred to as the diagnostic chart as it allows the clinician to quickly review ten parameters reflecting the hemodynamic state of the patient's cardiovascular system.

In the exemplary display of FIG. 9, the bar graphs are horizontal and the length of the bar graph in the horizontal direction represents the magnitude of the corresponding parameter.

As illustrated in FIG. 9, the bar graphs are labeled with the abbreviations for each of the parameters, as introduced above. In addition, in order to assist the clinician in quickly perceiving the significance of parameter that is outside the indicated normal range, the bar graphs preferably include a translation of the various parameters into more readily understood terms. The cardiac index (CI) is referred to as the GLOBAL FLOW and has the dimensions of liters/min/m$^2$.

Four of the parameters relate to the pump performance. The stroke index (SI) is referred to as the PUMP PERFORMANCE and has the dimensions of milliliters/m$^2$. One modulator that affects pump performance is the end diastolic index (EDI) which is referred to as the PRELOAD and has the dimensions of milliliters/m$^2$. The index of contractility (IC) and the acceleration index (ACI) are both shown as CONTRACTILITY parameters. The index of contractility is dependent upon fluid volume and has the dimensions 1/sec. The acceleration index is dependent upon the inotropic state of the patient's vasculature system and has the dimensions of 1/sec$^2$. The systemic vascular resistance index (SVRI) is referred to as the AFTERLOAD of the heart and has the dimensions of fluid ohms/m$^2$.

The left cardiac work index (LCWI) is referred to as the CARDIAC WORK and represents the amount of work the The left cardiac work index has the dimensions of kg.m/m$^2$.

The ejection fraction (EF) is referred to a the PUMP EFFICIENCY and is expressed as a percentage.

In the preferred embodiments of the present invention, the thoracic fluid index (TFI) from the NCCOM®3-R7 is inverted and displayed as thoracic fluid conductivity (TFC) (i.e., TFC=1/TFI). The thoracic fluid conductivity has a normal range of 0.030 to 0.050 mhos (i.e., 1/ohms). In FIG. 9, the thoracic fluid conductivity is referred to as the THORACIC FLUIDS. By using the conductivity, increasing amount of fluids results in increased conductivity and thus results in a shift in the bar graph to the right. Thus, the clinician perceives an increase (movement to the right) of the bar graph as an increase in the patient's fluids.

The mean arterial blood pressure (MAP) is displayed as the lowermost bar graph in FIG. 9 and is dimensioned in Torr.

As illustrated, the magnitude of each of the foregoing parameters is displayed both as a numeric value and as a length on the corresponding bar graph. The bar graph for each of the parameters further includes a pair of lines perpendicular to the bar graph (i.e., a pair of vertical lines 380 and 382, as illustrated for the bar graph for the cardiac index) which delineate the range of "normal" values for the parameter. (It should be understood that on a video display monitor, the vertical lines can be highlighted with a different color or brightness level so that they are more readily discernible.) For example, the bar graph for the cardiac index (CI) is shown as having the first vertical line 380 at a magnitude of 2.8 liters/min/m$^2$, representing the lower limit of the "normal" range, and having the second vertical line at a magnitude of 4.2 liters/min/m$^2$, representing the upper limit of the "normal" range. Thus, a clinician can easily determine which of the parameters are outside the normal range. For example in FIG. 9, it can be seen that the magnitudes of the systemic vascular resistance index (SVRI) and the mean arterial blood pressure are greater than the normal ranges for those parameters, and the magnitudes of the cardiac index (CI) and the index of contractility (IC) are less the normal range. In contrast the remaining six parameters are within their normal ranges.

Preferably, the bar graphs representing the parameters are scaled soazxc that the vertical lines for each of the bar graphs, with the exception of the mean arterial pressure bar graph, are vertically aligned with respect to each other, as illustrated in FIG. 9, to assist the clinician in quickly recognizing which of the parameters are above or below their respective "normal" ranges. Because of the large magnitude in the range of the mean arterial blood pressure, the vertical lines representing its "normal" limits are not aligned with the vertical lines of the other parameters.

The heart rate (HR), the patient's height, patient's weight and patient's date of birth are displayed in the display format of FIG. 9 as numeric parameters without corresponding bar graphs. The display format can also include other patient identification information and data storage identification.

When the computer 140 enters the activity block 378, it provides the alternative primary display illustrated in FIG. 10, which displays the hemodynamic status of the patient's cardiovascular system. Unlike the display of FIG. 9, the display of FIG. 10 provides an alphanumeric display of five of the above-described parameters, namely the cardiac index (CI), the mean arterial blood pressure (MAP), the left cardiac work index (LCWI), the systemic vascular resistance index (SVRI) and the heart rate (HR).

The display of FIG. 10 is distinguished from the display of FIG. 9 in that the cardiac index (CI) and the mean arterial blood pressure (MAP) are also displayed as a cartesian graph. The cardiac index is on the X-axis (i.e., the horizontal axis) and the mean arterial blood pressure is on the Y-axis (i.e., the vertical axis). The cartesian graph of FIG. 10 generally corresponds to the graphs of FIGS. 1, 2 and 3, and has an ellipse 400 that represents the range of normal combinations of magnitudes of the cardiac index and the mean arterial blood pressure. In FIG. 10, the ellipse 400 has a center 404 (i.e., the intersection of its major and minor axes) at a cardiac index of 3.5 liters/min/m$^2$, and at a mean arterial blood pressure of 92 Torr.

In addition to the ellipse 400, the cartesian graph of FIG. 10 includes a first curve 410 and a second curve 414 (both shown as dotted lines) that intersect at the center 404 of the ellipse 480. The curve 410 represents the normal left cardiac work index (LCWI), which in the display of FIG. 10 is equal to approximately 4.35 kg.m/m$^2$. The curve 414 represents the normal systemic vascular resistance index (SVRI), which in the display of FIG. 10 is equal to approximately 2030 fluidic ohms per square meter.

The cartesian graph of FIG. 10 further includes an indicator 420 that represents the patient's cardiac index and the patient's mean arterial blood pressure, and also represents the patient's left cardiac work index and exemplary systemic vascular resistance index. As illustrated for an FIGS. 9 and 10, the patient's cardiac index (CI) is 2.7 liters/min/m$^2$, which is below the normal range of values; and the patient's mean arterial blood pressure is 135 Torr which is considerably above the normal range of values. In addition, the patient's left cardiac work index (LCWI) is 5.0 kilograms per square meter, which is at the high end of the normal range for that parameter. The patient's systemic vascular resistance index (SVRI) is 3870 fluidic ohms/m$^2$, which is considerably greater than the normal range. By observing the position of the indicator 420 with respect to the ellipse 400 and with respect to the first curve 410 and the second curve 414, the clinician can readily perceive which of the four parameters differ from the normal values for the parameters.

In order to assist the clinician in quantitatively analyzing the displayed data, the display of FIG. 10 further includes an alphanumeric display of the percentage deviation of the calculated left cardiac work index and the systemic vascular resistance index from the normal values and indicates whether the parameters are greater than or less than the normal values. For example, in FIG. 10, the left cardiac work index is approximately 15 percent below a normal value of approximately 4.35 kg.m/m$^2$, which represents relative hypervolemia or relative hyperinotropy. The systemic vascular resistance index is 91 percent above a normal value of approximately 2030 dyn.sec/cm5m$^2$ (i.e., 2030 F.Ohms/m$^2$), which represents relative hypocapacitance.

The cartesian graph display of FIG. 10 is referred to as the therapeutic management chart. The clinician can use the information displayed in the therapeutic management chart of FIG. 10 in combination with the diagnostic chart of FIG. 9 to determine a proper course of therapy, as discussed above in connection with FIGS. 1, 2 and 3. For example, the clinician will observe that the patient will require therapy that increases the patient's arterial capacitance to reduce the systemic vascular resistance index. In addition, the patient will likely require therapy that increases either or both the patient's fluid volume or the patient's inotropy. For example, the acceleration index (ACI) parameter in FIG. 9 indicates that the patient's inotropic state is substantially normal. In contrast, the volume-dependent index of contractility (IC) parameter is below normal and indicates that the patient is hypovolemic. Thus, the proper therapy for the exemplary patient having these parameters should be increase the patient's fluid volume. This is consistent with the bar graph of the thoracic fluid conductivity in FIG. 9 which is at the low end of the normal range.

As discussed above, the end goal of the therapy is not always necessarily within the normal ranges of the displayed parameters. For example, a patient recovering from major surgery or certain illnesses may require additional oxygen to assure successful recovery. The clinician can use the displays of FIGS. 9 and 10 to determine a course of treatment in which the cardiovascular system is operated with parameters outside the normal range to enhance the patient's recovery. For example, it is preferable that a post-surgical course of therapy include a modality to cause the patient to be relatively hypervolemic to increase the oxygen-carrying capability of the patient's system. In preferred embodiments of the present invention, the clinician can select an alternative display mode in which the "normal" cardiac index, systemic vascular resistance index and left cardiac work index are adjusted to set a new goal for the patient's volume/inotropy and the patient's arterial capacitance in accordance with results of the study by W. C. Shoemaker. In other words, a goal is set to increase the oxygen perfusion of the tissues. This is illustrated in FIGS. 11 and 12 which illustrate two exemplary cartesian displays for the same patient.

Figure 11:
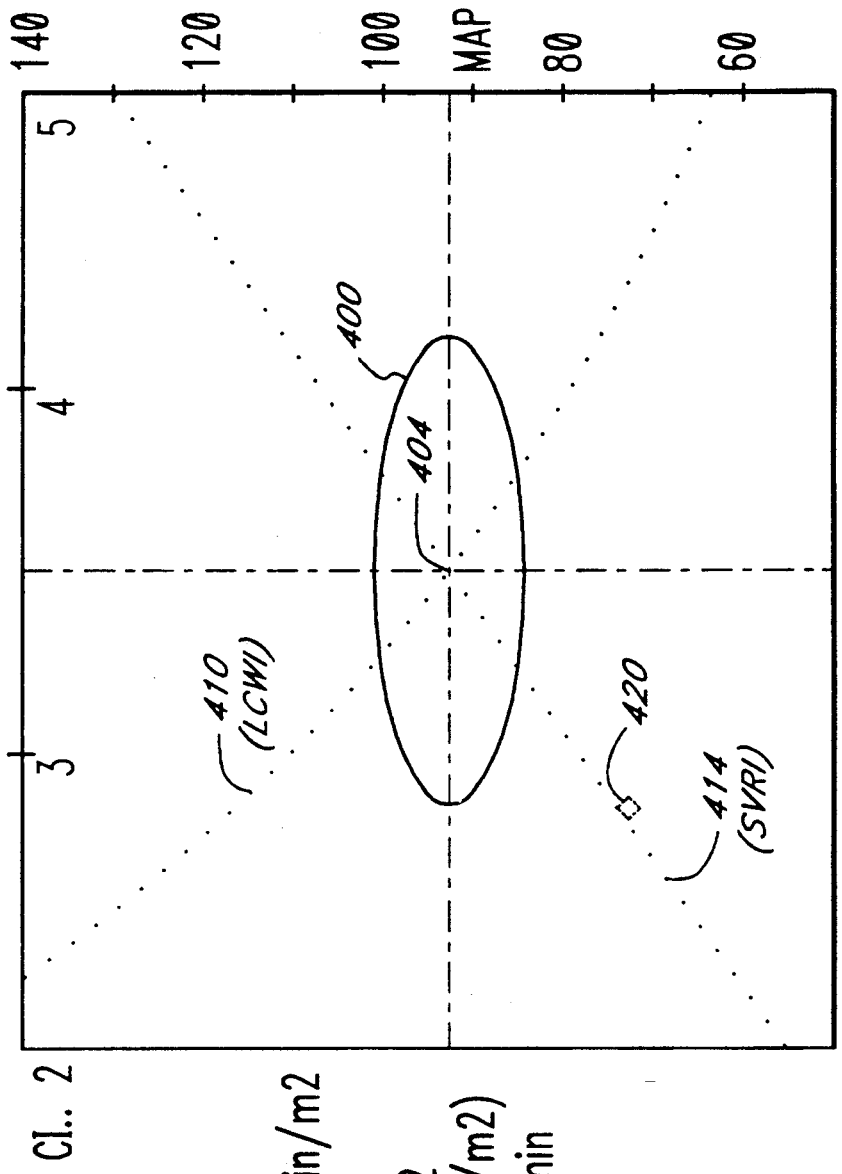
FIG. 11 illustrates the cartesian graph screen display of FIG. 10 for a patient having 43% relative hypovolemia and/or hypoinotropy and arterial normocapacitance.

In FIG. 11, the above-described normal ranges for the cardiac index, the systemic vascular resistance index and the left cardiac work index are used to define the ellipse 400, the first curve 410 and the second curve 414. The measured parameters are displayed alphanumerically to the left of the graph and the indicator 420 is located to show that the blood pressure is low, the cardiac index is low, the left cardiac work index is low (indicating either relative hypovolemia and/or relative hypoinotropy), and that the systemic vascular resistance index is "normal" (indicating normocapacitance). Thus, the indicated therapy would be to increase the volume and/or the inotropy. The location of the indicator 420 on the normocapacitance curve does not indicate any therapy related to the capacitance.

FIG. 11 should be contrasted with FIG. 12 which illustrates the same parameters for a patient recovering from surgery, or the like. The "normal" values for the cardiac index, the systemic vascular resistance index and the left cardiac work index have been adjusted upward in FIG. 12 to represent a therapeutic goal that will result in increased oxygen perfusion of the tissues. For example, the normal range of the cardiac index (CI) is shown as being approximately 3.8 to 5.2 liters/min/m$^2$ rather than 2.8 to 4.2 liters/min/m$^2$. Similarly, a curve 410, for the left cardiac work index (LCWI), representing the "normovolemia/normoinotropic," condition has been shifted to approximately 5.55 kg.m/m$^2$; and a curve 414, for the systemic vascular resistance index, representing the "normocapacitance" condition has been shifted to approximately 2690 F.Ohms/m$^2$ (2690 dyn.sec/cm5m$^2$). Thus, as illustrated by the location of the indicator 420' in FIG. 12, the post-operative patient is 55 percent relatively hypovolemic and the therapeutic modality to expand the patient's fluid volume should be increased with respect to the corresponding treatment for the normal goals illustrated in FIG. 11. At the same time, the patient should be vasodilated in response to the 26 percent relative hypocapacitance according to the new system vascular resistance index goal in order to increase the intravascular space for the acceptance of additional fluids.

As set forth above, the electronic system of the present invention preferably includes the printer 146. The printer is preferably capable of printing graphic images of the screen displays of FIGS. 9 and 10 to provide a permanent record of the screen displays so that they may be compared to analyze the results of a course of therapy over a period of time. In addition, the computer 140 preferably includes long term data storage capabilities (i.e., a hard disk drive and/or a floppy disk drive) so that the data collected during a diagnostic session can be saved and displayed contemporaneously with the data collected during a current diagnostic session. Thus, the clinician can observe the results of the previously prescribed therapy and modify the therapy, as needed, in order to achieve the desired end results.

Although this invention has been described in terms of certain preferred embodiments, other embodiments that are apparent to those of ordinary skill in the art are also within the scope of this invention. Accordingly, the scope of the invention is intended to be defined only by reference to the appended claims.

What is claimed is:

1. A method of achieving a preselected hemodynamic state in a subject mammal comprising the steps of:
   (a) determining the subject's mean arterial pressure (MAP);
   (b) measuring the subject's cardiac index (CI);
   (C) determining the subject's left cardiac work index (LCWI) utilizing the measured MAP and CI values according to the formula:

$$LCWI = (MAP - PAOP) \times CI \times K$$

wherein PAOP represents pulmonary artery occluded pressure and K is a constant;
   (D) determining the subject's systemic vascular resistance index utilizing the measured MAP and CI values according to the formula:

$$SVRI = \left( \frac{MAP - CVP}{CI} \right) \times L$$

wherein SVRI represents the systemic vascular resistance index, CVP is central venous pressure and L is a constant;
   (E) preselecting a desired hemodynamic state, defined by desired values for LCWI and SVRI;
   (F) determining the percentage deviation of the subject's determined values for LCWI above or below the desired value for LCWI;
   (G) determining the percentage deviation of the subject's determined values for SVRI above or below the desired value for SVRI:
   (H) administering a therapeutic doses of pharmacologically active materials for altering the LCWI and SVRI values to achieve in the subject the preselected hemodynamic state.

2. A method of achieving a preselected hemodynamic state as in claim 1, wherein the subject is an adult human.

3. A method of achieving a preselected hemodynamic state as in claim 2, wherein the preselected hemodynamic state comprises a systemic vascular resistance index of approximately 2030 dyn.sec/cm$^5$m$^2$, and a left cardiac work index of approximately 4.35 kg.m/m$^2$.

4. A method as in claim 3, wherein the pharmacologically active material comprises a vasodilator if the systemic vascular resistance index is greater than about 2030 dyn.sec/cm$^5$m$^2$.

5. A method as in claim 3, wherein the pharmacologically active material comprises a vasoconstrictor if the systemic vascular resistance index is less than about 2030 dyn.sec/cm$^5$m$^2$.

6. A method of achieving a preselected hemodynamic state as in claim 1, wherein the patient is an adult human and the preselected hemodynamic state comprises a systemic vascular resistance index within the range of from about 1700 to about 2650 dyn.sec/cm$^5$m$^2$.

7. A method of achieving a preselected hemodynamic state as in claim 1, wherein the patient is an adult human and the preselected hemodynamic state comprises a left cardiac work index within the range of from about 3.3 to about 5.3 kg.m/m$^2$.

8. A method of achieving a preselected hemodynamic state as in claim 1, wherein the patient is a neonatal infant human and the preselected hemodynamic state comprises a systemic vascular resistance index within the range of from about 950 to about 1500 dyn.sec/cm$^5$m$^2$.

9. A method of achieving a preselected hemodynamic state as in claim 1, wherein the patient is a neonatal human infant and the preselected hemodynamic state comprises a left cardiac work index within the range of from about 2.5 to about 4.0 kg.m/m$^2$.

10. The method of claim 1, further comprising:
    (i) measuring the subject's acceleration index (ACI);
    (ii) preselecting a desired inotropic state, consisting of a value of ACI;
    (iii) determining the percentage deviation of the subject's measured value for ACI from the preselected value of ACI;
    (iv) subtracting the determined percentage deviation of ACI from the percentage deviation of LCWI determined in step (F) in order to give an indication of the percentage of hypervolemia or hypovolemia;
    (v) administering a therapeutic dose of pharmacologically active material or an amount of fluid for bringing the percentage of hypervolemia or hypovolemia to achieve in the subject the preselected volemic state.

11. The method of claim 10, wherein the subject is an adult human and the preselected inotropic state comprises an ACI measurement within the range of from about 0.5/sec$^2$ to about 1.5/sec$^2$.

12. The method of claim 11, wherein the preselected inotropic state comprises an ACI measurement of about 1.0sec$^2$.

13. The method of claim 10, wherein the percentage deviation in ACI is substantially equal to the percentage deviation of LCWI and the one or more pharmacologically active materials for bringing the percentage deviation of LCWI to substantially zero administered in step (H) comprises a pharmacologically active material for affecting inotropic state.

14. The method of claim 13, wherein the pharmacologically active material for affecting inotropic state comprises a negative inotropic.

15. The method of claim 10, wherein the percentage deviation in ACI is substantially zero, and the one or more pharmacologically active materials for bringing the percentage deviation of LCWI to substantially zero administered in step (H) comprises a pharmacologically active material for affecting volemia.

16. The method of claim 15, wherein pharmacologically active material for affecting volemia comprises a diuretic agent.

17. The method of claim 10, wherein the percentage deviation of LCWI determined in step (F), the percentage deviation of SVRI determined in step (G), and the difference between the percentage deviation of ACI and the percentage deviation of LCWI determined in step (iv) are all larger than substantially zero, and wherein the pharmacologically active materials administered in step (H) comprise:
    a pharmacologically active material for affecting inotropy;
    a pharmacologically active material for affecting volemia; and
    a pharmacologically active material for affecting vasoactivity.

18. The method of claim 1, wherein the percentage deviation in LCWI is substantially zero, and the one or more pharmacologically active materials administered in step (H) comprises a pharmacologically active material for affecting vasoactivity.

19. The method of claim 18, wherein the pharmacologically active material for affecting vasoactivity comprises a vasodilator or an ACI inhibitor.

20. The method of claim 1, wherein the values for PAOP and CVP are assumed to have their values for a normal supine resting adult.

21. A method of achieving a preselected hemodynamic state in a mammal, comprising the steps of:
determining means arterial pressure in the mammal;
measuring cardiac index in the mammal;
measuring acceleration index in the mammal;
determining a first deviation, if any, from a preselected volemic state;
determining a second deviation, if any, from a preselected capacitive state;
determining a third deviation, if any, from a preselected inotropic state; and
administering a therapeutic dose of at least one pharmacologically active material for altering the first, second and third deviations to achieve a preselected hemodynamic state.

22. A method of achieving a preselected hemodynamic state as defined in claim 21, wherein the preselected volemic state is normovolemia.

23. A method of achieving a preselected hemodynamic state as defined in claim 22, wherein the volemic state is measured as the left cardiac work index and ranges from approximately 3.3 to 5.3 kg.m/m$^2$.

24. A method of achieving a preselected hemodynamic state as defined in claim 21, wherein the preselected capacitive state is normocapacitance.

25. A method of achieving a preselected hemodynamic state as defined in claim 21, wherein the preselected hemodynamic state comprises normovolemia, normoinotropy and arterial normocapacitance.

26. A method of achieving a preselected hemodynamic state as defined in Claim 21, wherein the preselected hemodynamic state comprises a mean arterial pressure of from about 84 to about 100 Torr.

27. A method of achieving a preselected hemodynamic state as defined in Claim 21, further comprising the step, prior to the administering step, of selecting a pharmacologically active material for reducing the deviation from the preselected volemic state.

28. A method of achieving a preselected hemodynamic state as defined in Claim 21, wherein the mammal is a human adult in postoperative recovery and the preselected hemodynamic state comprises normotension and hyperdynamic global blood flow.

29. A method of determining and correcting deviations from normodynamic circulation, consisting of normovolemia, normovasoactivity and normoinotropy, in a subject mammal, comprising the steps of:
(a) determining the subject's mean arterial pressure (MAP);
(b) measuring the subject's cardiac index (CI);
(c) determining the subject's left cardiac work index (LCWI) utilizing the measured MAP and CI values according to the formula:

$$LCWI = (MAP - PAOP) \times CI \times K$$

wherein PAOP is the pulmonary artery occluded pressure and K is a constant;

(d) determining a first deviation from normal LCWI by utilizing the determined value for LCWI according to the formula:

$$\text{deviation} = \frac{LCWI}{\text{normal } LCWI}$$

(e) measuring the subject's acceleration index (ACI);
(f) determining a second deviation from normoinotropy by utilizing the measured value for ACI according to the formula:

$$\text{deviation} = ACI/\text{normal } ACI$$

(g) determining a third deviation from normovolemia, comprising subtracting the second deviation from the first deviation;
(h) determining the subject's systemic vascular resistance index utilizing the measured MAP and CI values according to the formula:

$$SVRI = \frac{(MAP - CVP) \times L}{CI}$$

wherein SVRI represents the systemic vascular resistance index, CVP is central venous pressure and L is a constant;
(i) determining a fourth deviation from normovasoactivity by utilizing the determined value for SVRI according to the formula:

$$\text{deviation} = \frac{SVRI}{\text{normal } SVRI}$$

(j) increasing fluid volume if the third deviation is not substantially zero and the first deviation is less than 1.0, and decreasing fluid volume if the third deviation is not substantially zero and the first deviation is greater than 1.0;
(k) causing vasodilation in the subject if the fourth deviation is greater than 1.0, and causing vasorestriction if the fourth deviation is less than 1.0; and
(l) causing a negative inotropic effect in the subject if the second deviation is greater than 1.0, and causing a positive inotropic effect in the subject if the second deviation is greater than 1.0.

30. The method of claim 29, wherein steps (j), (k) and (l) each comprise the administration to the subject of a pharmacologically active material.

31. The method of claim 30, wherein each of steps (a) through (l) is repeated one or more times for the same subject, and wherein the amount pharmacologically active material administered each subsequent time the steps are repeated is increased or decreased until the difference of each of the determined deviation from 1.0 is substantially zero.

32. A method of determining and correcting deviations from normovasoactivity in a subject mammal, comprising the steps of:
(a) determining the subject's mean arterial pressure (MAP);
(b) measuring the subject's cardiac index (CI);
(c) determining the subject's systemic vascular resistance index utilizing the measured MAP and CI values according to the formula:

$$SVRI = \frac{(MAP - CVP) \times L}{CI}$$

wherein SVRI represents the systemic vascular resistance index, CVP is central venous pressure and L is a constant;

(d) determining a deviation from normovasoactivity by utilizing the determined value for SVRI according to the formula;

$$deviation = \frac{SVRI}{normal\ SVRI}$$

and;

(e) administering a pharmacologically vasoconstrive material if the deviation is less than one, and administering a pharmacologically vasocilating material if the deviation is greater than one.

33. The method of claim 32, additionally comprising repeating each of steps (a) through (e) one or more times in the same subject; and increasing the amount of pharmacologically vasoconstrictive material if the deviation remains less than one, decreasing the amount of pharmacologically vasoconstrictive material if the deviation changes from less than one to greater thân one, increasing the amount of pharmacologically vasodilating material if the deviation remains greater than one, and decreasing the amount of pharmacologically vasodilating material if the deviation changes from greater than one to less than one.

34. A method of determining deviations from normodynamic circulation, consisting of normoinotropy, normovolemia and normovasoactivity in a subject mammal, comprising:

(a) determining the subject's mean arterial pressure (MAP);
(b) measuring the subject's cardiac index (CI);
(c) determining the subject's left cardiac work index (LCWI) utilizing the measured MAP and CI values according to the formula:

LCWI=(MAP−PAOP)×CI×K wherein PAOP is the pulmonary artery occluded pressure and K is a constant;
(d) determining a deviation (1) from normal LCWI by utilizing the determined value for LCWI according to the formula:

$$deviation\ (1) = \frac{LCWI}{normal\ LCWI}$$

(e) measuring the subject's acceleration index (ACI):
(f) determining the deviation (2) in inotropy from normoinotropy by utilizing the measured value for ACI according to the formula:

deviation (2)=ACI/normal ACI (g) determining the deviation (3) in volemia from normovolemia, comprising subtracting deviation (2) from deviation (1);
(h) determining the subject's systemic vascular resistance index utilizing the measured MAP and CI values according to the formula:

$$SVRI = \frac{(MAP - CVP) \times L}{CI}$$

wherein SVRI represents the systemic vascular resistance index, CVP is central venous pressure and L is a constant; and
(i) determining deviation (4) in vasoactivity from normovasoactivity by utilizing the determined value for SVRI according to the formula:

$$deviation\ (4) = \frac{SVRI}{normal\ SVRI}.$$

35. A method of determining and correcting devaitions from normovolemia in a subject mammal, comprising the steps of:

(a) determining the subject's mean arterial pressure (MAP);
(b) measuring the subject's cardiac index (CI);
(c) determining the subject's left cardiac work index (LCWI) utilizing the measured MAP and CI values according to the formula:

LCWI=(MAP−PAOP)×CI×K wherein PAOP is the pulmonary artery occulded pressure and K is a constant;
(d) determining a first deviation from normal LCWI by utilizing the determined value for LCWI according to the formula:

$$deviation = \frac{LCWI}{normal\ LCWI}$$

(e) measuring the subject's acceleration index (ACI);
(f) determining a second deviation from normoinotropy by utilizing the measured value for ACI according to the formula:

deviation=ACI/normal ACI (g) determining a third deviation from normovolemia, comprising subtracting the second deviation from the first deviation; and
(h) increasing fluid volume if the third deviation is zero or negative and the first deviation is less than 1.0, and decreasing fluid volume if the third deviation is zero or positive and the first deviation is greater than 1.0.

36. The method of any one of claims 35, 29 or 34 wherein normal LCWI is equal to 4.35 kg.m/m$^2$.

37. The method of any one of claim 35, 29 or 34 wherein normal ACI is equal to 1.0/sec$^2$.

38. The method of any one of claim 29, 32 or 34 wherein normal SVRI is equal to 2030 hyn.sec/cm$^5$m$^2$.

* * * * *

UNITED STATES PATENT AND TRADEMARK OFFICE
CERTIFICATE OF CORRECTION

PATENT NO. : 5,103,828
DATED : April 14, 1992
INVENTOR(S) : Bohumir Sramek

It is certified that error appears in the above-indentified patent and that said Letters Patent is hereby corrected as shown below:

In Column 4, at line 64, before "instrument" add --continuously monitor cardiac output through the use of an--.

In Column 8, at line 21, after "Figure" insert --1--.

In Column 9, at line 6, after "vasoconstricted" insert --arterial bed--.

In Column 12, at line 45, change "12" to --112--.

In Column 28, at line 11, change "of" to --for--.

In Column 28, at line 42, change "inotropic" to --inotrope--.

In Column 29, at line 27, change "normovolemia" to --normovolemic--.

Signed and Sealed this

Seventeenth Day of August, 1993

Attest:

BRUCE LEHMAN

*Attesting Officer*    *Commissioner of Patents and Trademarks*